(12) United States Patent
Laukkanen et al.

(10) Patent No.: US 11,389,537 B2
(45) Date of Patent: *Jul. 19, 2022

(54) DRUG DELIVERY SYSTEM FOR SUSTAINED DELIVERY OF BIOACTIVE AGENTS

(71) Applicant: UPM-Kymmene Corporation, Helsinki (FI)

(72) Inventors: Antti Laukkanen, Helsinki (FI); Ruzica Kolakovic, Helsinki (FI); Leena Peltonen, Klaukkala (FI); Timo Laaksonen, Espoo (FI); Jouni Hirvonen, Vantaa (FI); Heikki Lyytikainen, Naantali (FI); Harri Jukarainen, Kuusisto (FI); Prijo Kortesuo, Parainen (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 14/358,141

(22) PCT Filed: Nov. 15, 2012

(86) PCT No.: PCT/FI2012/051121

§ 371 (c)(1),
(2) Date: May 14, 2014

(87) PCT Pub. No.: WO2013/072563

PCT Pub. Date: May 23, 2013

(65) Prior Publication Data

US 2014/0322327 A1    Oct. 30, 2014

(30) Foreign Application Priority Data

Nov. 15, 2011  (FI) .................................... 20116138

(51) Int. Cl.
*A61K 47/38* (2006.01)
*A61K 9/00* (2006.01)
(Continued)

(52) U.S. Cl.
CPC ............ *A61K 47/38* (2013.01); *A61K 9/0019* (2013.01); *A61K 9/0034* (2013.01);
(Continued)

(58) Field of Classification Search
None
See application file for complete search history.

(56) References Cited

U.S. PATENT DOCUMENTS 5,405,953 A * 4/1995 Banker ................. A01N 25/10
                                                    536/120
2002/0061335 A1  5/2002 Kumar
(Continued)

FOREIGN PATENT DOCUMENTS

CN    101172164 A    5/2008
FI     20106121 A    4/2012
(Continued)

OTHER PUBLICATIONS

Young "Comparison of properties of chemical cellulose pulps", Cellulose (1994)1, 107-130.*

(Continued)

*Primary Examiner* — Isis A Ghali
(74) *Attorney, Agent, or Firm* — Nixon Peabody LLP

(57) ABSTRACT

A drug delivery system for sustained delivery of bioactive agents, the system includes a matrix including nanofibrillated cellulose derived from plant based material and at least one bioactive agent, and at least one support selected from (Continued)

synthetic polymers, bio compounds and natural polymers. Also, methods for the manufacture of the system and methods of using it.

17 Claims, 11 Drawing Sheets

(51) Int. Cl.
| | |
|---|---|
| *A61K 9/50* | (2006.01) |
| *A61K 9/70* | (2006.01) |
| *A61K 9/16* | (2006.01) |
| *A61K 31/137* | (2006.01) |
| *A61K 31/216* | (2006.01) |
| *A61K 31/277* | (2006.01) |
| *A61K 31/405* | (2006.01) |
| *A61K 31/496* | (2006.01) |
| *A61K 31/573* | (2006.01) |

(52) U.S. Cl.
CPC .......... *A61K 9/1652* (2013.01); *A61K 9/5042* (2013.01); *A61K 9/70* (2013.01); *A61K 31/137* (2013.01); *A61K 31/216* (2013.01); *A61K 31/277* (2013.01); *A61K 31/405* (2013.01); *A61K 31/496* (2013.01); *A61K 31/573* (2013.01)

(56) References Cited

U.S. PATENT DOCUMENTS

| | | | |
|---|---|---|---|
| 2009/0221047 A1* | 9/2009 | Schindler | B01D 39/04 435/160 |
| 2010/0159046 A1 | 6/2010 | Harris et al. | |

FOREIGN PATENT DOCUMENTS

| | | |
|---|---|---|
| JP | H04243819 A | 8/1992 |
| JP | H10248872 A | 9/1998 |
| JP | 2006-160626 A | 6/2006 |
| JP | 2006-160627 A | 6/2006 |
| JP | H10248872 A | 8/2009 |
| JP | 2014520817 A | 8/2014 |
| WO | 02/22172 A2 | 3/2002 |
| WO | 2007/027849 A2 | 3/2007 |
| WO | 2009084566 A1 | 7/2009 |
| WO | 2010080264 A1 | 7/2010 |
| WO | 2010/142850 A1 | 12/2010 |
| WO | 2012056111 A2 | 5/2012 |
| WO | 2013/006729 A2 | 1/2013 |

OTHER PUBLICATIONS

Zimmermann et al. "Properties of nanofibrillated cellulose from different raw materials and its reinforcement potential", Carbohydrate Polymers 79 (2010) 1086-1093.*
Sannino et al. "Biodegradable Cellulose-based Hydrogels: Design and Application", Materials, 2009, 2, 353-373.*
Paakko et al. "Long and entangled native cellulose I nanofibers allow flexible aerogels and hierarchically porous template for functionalities", Soft Matter, 2008, 4, 2492-2499. (Year: 2008).*
Klemm et al. "Nanocellulose: A New Family of Nature-Based Materials", Ayngew. Chem. Int. Ed., 50, 5438-5466, May 20, 2011 (Year: 2011).*
Hanna Valo et al.: "Immobilization of protein-coated drug nanoparticles in nanofibrillar cellulose matrices—Enhanced stability and release", Journal of Controlled Release, vol. 156, No. 3, Jul. 23, 2011 (Jul. 23, 2011), pp. 390-397, XP55025318, ISSN: 0168-3659, 001: 10.1016/j.jconrel.2011.07.016 points 2.1-2.9, Cited in FI Search Report and ISR.
Eliane Trovatti et al.: "Biocellulose Membranes as Supports for Dermal Release of Lidocaine", Biomacromolecules, vol. 12, No. 11, Oct. 16, 2011 (Oct. 16, 2011), pp. 4162-4168, XP55025497, ISSN: 1525-7797, 001: 10.1021/bm201303r experimental section, Cited in FI Search Report and ISR.
International Search Report, dated Feb. 14, 2013, from corresponding PCT application.
Finnish Search Report, dated Aug. 3, 2012, from corresponding FI application.
Finnish Office Action in Finnish Patent Application No. FI 20116138, dated Feb. 11, 2021 (4 pages).
Wikipedia, "Nanocellulose," Retrieved from the internet on Feb. 1, 2021, <URL: https://en.wikipedia.org/wiki/Nanocellulose/> (4 pages).
James L. Minor: "Hornification—Its Origin and Meaning", Recycling 101, Progress in Paper Recycling, vol. 3, No. 2, Feb. 1994, pp. 93-95.

* cited by examiner

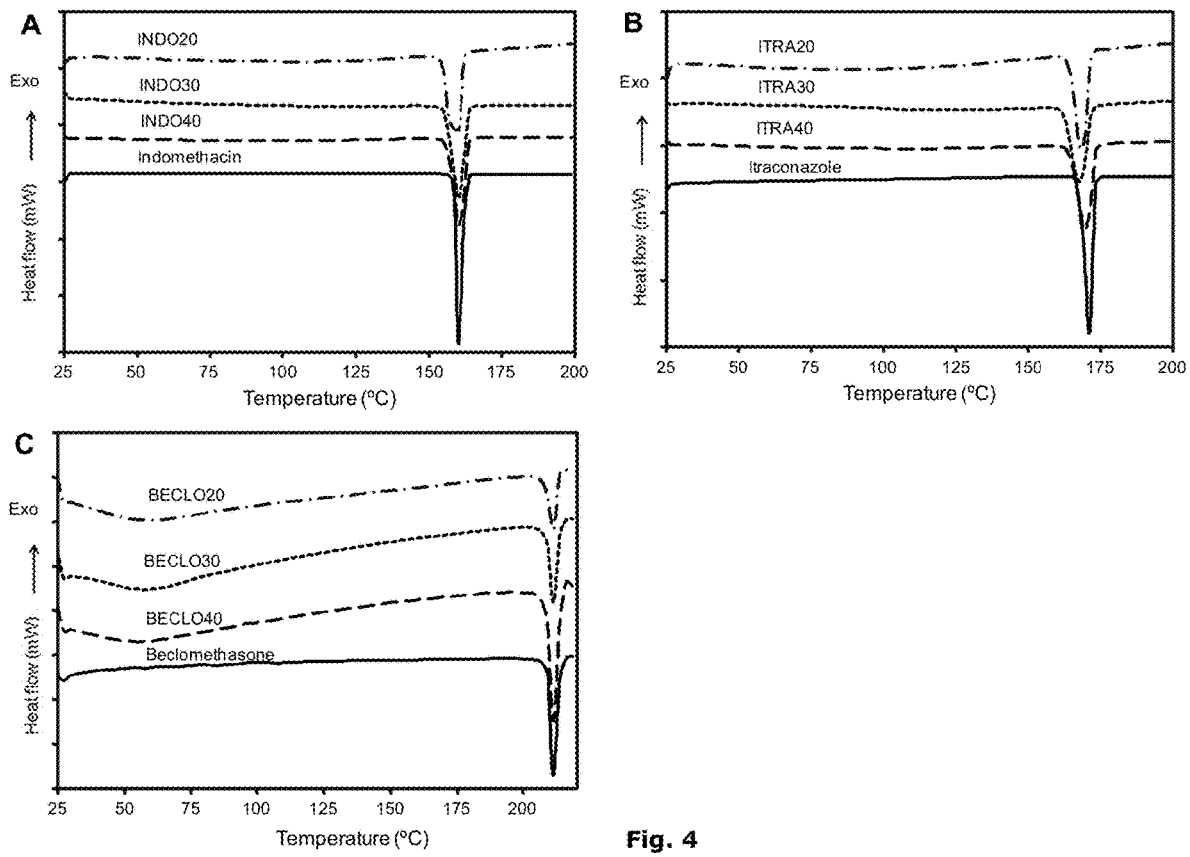
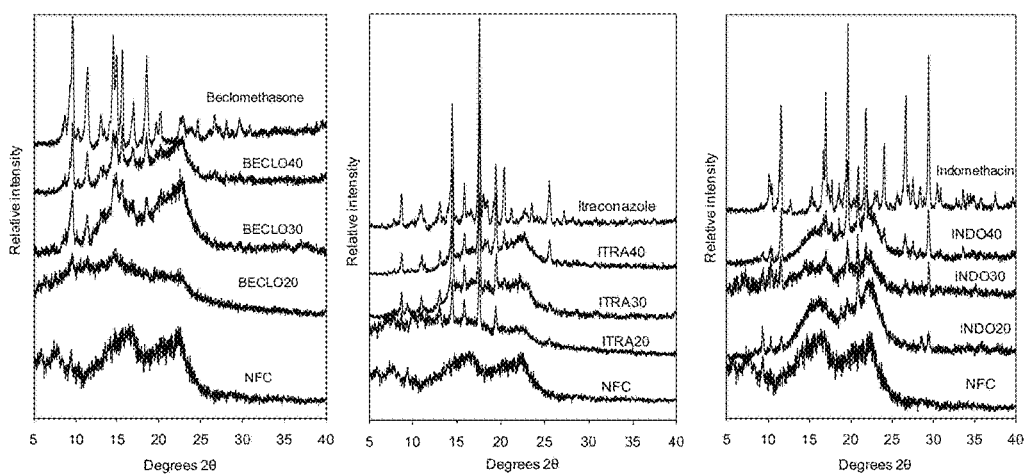
Fig. 5

DRUG DELIVERY SYSTEM FOR SUSTAINED DELIVERY OF BIOACTIVE AGENTS

FIELD OF THE INVENTION

The invention relates to new applications of nanofibrillated cellulose in the field of drug delivery, particularly to new polymeric drug delivery systems. The invention deals with matrices comprising nanofibrillated cellulose, for sustained delivery of bioactive agents, with devices and delivery systems comprising said matrices and with methods for their manufacture. The invention also relates to the use of said matrices for sustained delivery of bioactive agents, particularly in medical devices, combination products and implants.

BACKGROUND

Drug delivery systems based on polymeric materials have widely been used for the sustained delivery of various bioactive agents.

Cellulose is the most commonly occurring natural polymer on the earth, and also one of the most interesting, naturally existing molecular structures. Microfibrils in nanofibrillated cellulose are composed of highly aligned crystalline β-D-(1-4)gluco-pyranose polysaccharide chains (cellulose I crystals) where the chains are strongly intermolecularly bound via a multitude of hydrogen bonds. This crystalline structure is responsible for its intrinsic strength and its relatively high chemical stability.

Different techniques have been developed in the last years particularly for the production of nanofibrillated cellulose, and in most cases, chemical, enzymatic or mechanical pre-treatments are needed in order to weaken the structure of the fiber walls before the isolation of the microfibres. Nanofibrillated cellulose (NFC) is typically obtained by disintegrating the ultrastructure of the cell wall while preserving the integrity of the microfibrils. Elementary fibrils and fibril bundles obtained in these ways have a typical diameter in the range of few nanometers and the length up to several micrometers.

NFC has been proposed for the generation of strong and tough nanopapers, nanocomposites where small contents of NFC are added to polymeric matrices, robust foams and aerogels, and also for pharmaceutical applications.

WO 2010142850 publication describes a product of solid particles, wherein each particle comprises an active agent in a hydrophobic core, which core is at least partially coated with a hydrophobic agent. These particles can further be combined with nanofibrillated cellulose.

WO 2007027849 publication is related to methods and compositions for the manufacture and use of NFC derived from bacterial nanocellulose, for use in a wound healing system, and particularly as a wound dressing for a wide variety of wound types, locations, shapes, depth and stage(s) of healing. The wound dressing may include one or more active substances that promote wound healing.

In current drug delivery systems and particularly in intrauterine delivery systems and implants, systems based on polydimethylsiloxane and ethylenevinylacetate copolymers are widely used. Said systems are particularly suitable for hydrophobic and relatively small drug molecules and in the systems the drug is typically incorporated in the polymer matrix reservoir.

The use of polymeric delivery systems of bioactive agents exhibits significant advantages as a method of continuous administration of bioactive agents to maintain fixed plasma levels. Therefore there is a constant need for development in the field of polymer science and technology that would lead to the construction of novel materials for use in sustained delivery of bioactive agents.

Accordingly, there is an evident need for new and improved materials and matrices which are applicable to various bioactive agents including hydrophobic and hydrophilic drugs, as well as bioactive proteins and peptides, for providing sustained delivery of said agents.

SUMMARY

Aspects of the invention are directed to a matrix for sustained delivery of bioactive agents, said matrix comprising nanofibrillated cellulose and at least one bioactive agent.

Further aspects of the invention are directed to new drug delivery systems for sustained delivery of bioactive agents, comprising said matrix, said systems providing for extended applicability of the currently available systems and devices.

Further aspects of the invention are directed to devices, systems and formulation for sustained delivery of bioactive agents, comprising said matrix incorporated in at least one polymeric support or reservoir. Suitably the device is a medical device or implant.

Still further aspects of the invention are directed to transdermal patches for sustained delivery of bioactive agents, said patches comprising the matrix incorporated in or on at least one support.

Still further aspects of the invention are directed to the use of the matrix in systems, formulations and medical devices and combinations products, for sustained delivery of bioactive agents.

Further aspects of the invention are directed to methods for the manufacture of said matrix, where any of the alternative methods A to D may be used:

Method A comprises the steps of blending at least one bioactive agent with an aqueous suspension or dispersion comprising nanofibrillated cellulose to obtain a mixture, followed by removal of water from the mixture and drying.

Method B comprises the steps of dissolving at least one bioactive agent in a solvent or buffer solution to obtain a solution, which is then blended with an aqueous suspension or dispersion comprising nanofibrillated cellulose to obtain a mixture, followed by spray drying the mixture.

Method C comprises the steps of mixing or dissolving at least one bioactive agent in a solvent or buffer solution to obtain a blend or solution, which is then mixed with an aqueous suspension or dispersion comprising nanofibrillated cellulose to obtain a mixture, which is introduced into a volume of organic extraction agent miscible with water, into the form of one or several elements, removing the elements and drying them.

Method D comprises the steps of introducing an aqueous suspension or dispersion comprising nanofibrillated cellulose into a volume of organic extraction agent miscible with water and comprising at least one bioactive agent, into the form of one or several elements, removing the elements and drying them.

Further aspects of the invention are directed to a method for the manufacture of drug delivery systems for sustained delivery of bioactive agents, said method comprising the steps of incorporating said matrix in or on at least one support.

Particularly, the ease of manufacture, applicability to various bioactive compounds, suitability for delivery systems providing up to several years sustained release of the bioactive agent, and avoiding challenges relating to fouling are some examples of the desired benefits achieved by the present invention.

The characteristic features of the invention are presented in the appended claims.

BRIEF DESCRIPTION OF THE DRAWINGS

FIG. 4 presents DSC curves of NFC/Itraconazole (B), NFC/Indomethacin (A) matrices and NFC/Beclomethasone dipropionate (C) matrices and corresponding pure drug.

FIG. 5 shows X-ray diffractograms of NFC/Indomethacin, NFC/Itraconazole and NFC/Beclomethasone matrices and corresponding pure drugs.

DEFINITIONS

Figure 1:
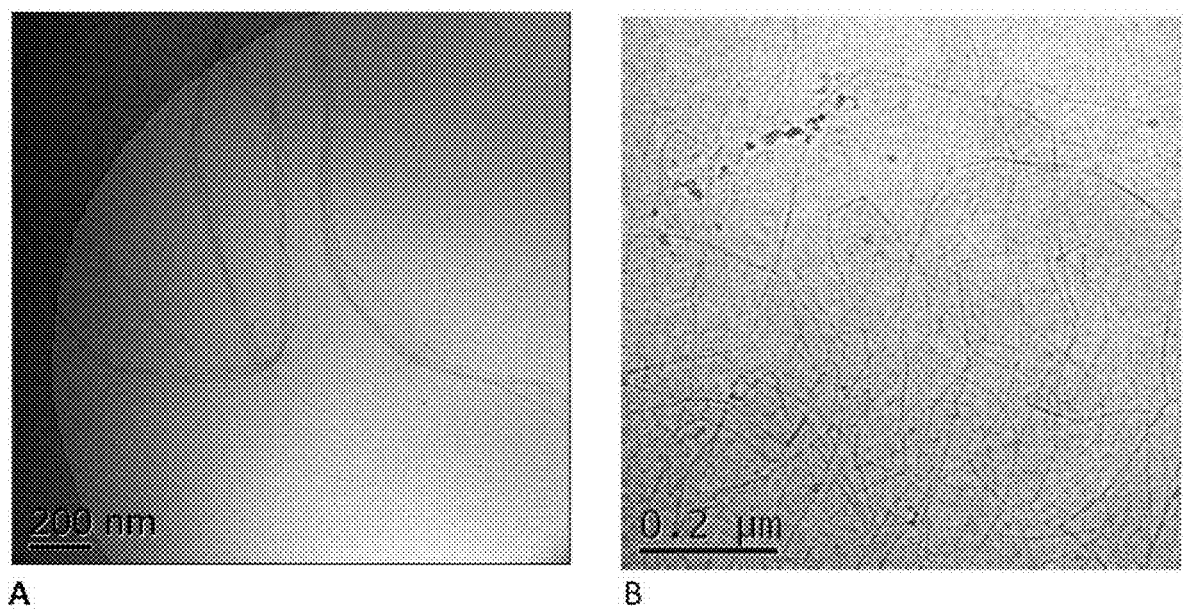
FIG. 1 depicts Cryo-TEM images of native NFC (A) and anionic NFC (B).

Unless otherwise specified, the terms, which are used in the specification and claims, have the meanings commonly used in the field of pharmaceuticals and drug delivery. Specifically, the following terms have the meanings indicated below.

The term "sustained delivery" or "sustained release" refer here to the delivery or release of a bioactive agent, such as a drug, at a predetermined rate by maintaining an essentially constant drug level for a specific period of time. The terms "controlled release" and "extended release" retarded relase, prolonged release, slow release ja rate controlled release are understood to be used for the same purpose.

The term "bioactive agent" refers here to a therapeutically active agent, a prophylactic agent, drug substance, medicament, peptide or protein.

As used herein, the term "nanofibrillated cellulose", (NFC) is understood to encompass all microfibrillated celluloses (MFC) and nanocelluloses. Further, there are several other widely used synonyms for fibril cellulose. For example: fibril cellulose, cellulose nanofiber, (CNF), nanofibrillar cellulose, nano-scale fibrillated cellulose, microfibrillar cellulose, or cellulose microfibrils. In addition, NFC produced by certain microbes has also various synonyms, for example, bacterial cellulose (BC), microbial cellulose (MC), biocellulose, nata de coco (NDC), or coco de nata (CDN).

DETAILED DESCRIPTION OF THE INVENTION

There exists a continuous demand for new sustained release drug delivery techniques. Slow release formulations are used for example in women's health care for contraception, menopause management and bleeding, as well as gynaecological therapies like treatment of fibroids and endometriosis. Often implants for subcutaneous delivery, as well as intrauterine and vaginal delivery systems are preferred means for sustained delivery. In implants, steady state release from few days to months and further to several years is often desirable. Existing polymer based delivery systems are typically not satisfactory alternatives for the delivery of e.g. oligomeric peptide or protein drugs or more hydrophilic drug compounds. It was surprisingly found that nanofibrillated cellulose (NFC) can be used for providing a matrix for sustained delivery of bioactive agent(s), wherein said matrix comprises nanofibrillated cellulose and at least one bioactive agent incorporated therein. The bioactive agent is suitably bound to or encapsulated in said matrix. Said matrix may suitably be incorporated in a system, medical device or implant for providing sustained delivery of the bioactive agent(s). Nanofibrillated cellulose suitably acts as a carrier of said bioactive agent.

Matrices based on NFC can be used for the release of bioactive agents, such as drug molecules in a controlled manner for predetermined and long periods of time. Desired diffusion kinetics such as close to zero order kinetics can be achieved with many bioactive agents, which is considered as a highly valuable feature particularly in implanted slow release devices.

Nanofibrillated cellulose (NFC) used in the present invention may be derived from any plant based material or it may be derived from any microbial cellulose.

The term "cellulose raw material" refers to any cellulose raw material source that can be used in production of cellulose pulp, refined pulp, and nanofibrillated cellulose. The cellulose raw material may be based on any plant material that contains cellulose.

Plant material may be wood and said wood can be from softwood tree such as spruce, pine, fir, larch, douglas-fir or hemlock, or from hardwood tree such as birch, aspen, poplar, alder, eucalyptus or acacia, or from a mixture of softwoods and hardwoods. Non-wood material can be from agricultural residues, grasses or other plant substances such as straw, leaves, bark, seeds, hulls, flowers, vegetables or fruits from cotton, corn, wheat, oat, rye, barley, rice, flax, hemp, manilla hemp, sisal hemp, jute, ramie, kenaf, bagasse, bamboo or reed.

The cellulose raw material may also be derived from the cellulose-producing micro-organism, such as from bacterial fermentation processes. The micro-organisms can be of the genus *Acetobacter, Agrobacterium, Rhizobium, Pseudomonas* or *Alcaligenes*, preferably of the genus *Acetobacter* and more preferably of the species *Acetobacter xylinum* or *Acetobacter pasteurianus*.

The term "cellulose pulp" refers to cellulose fibers, which are isolated from any cellulose raw material using chemical, mechanical, thermo-mechanical, or chemi-thermo-mechanical pulping processes. Cellulose pulp, which can be pulp of plant origin, especially wood (softwood or hardwood pulp, for example bleached birch pulp) and where the cellulose molecules are oxidized in one of the above-described methods, is easy to disintegrate to fibril cellulose.

The term "nanofibrillated cellulose" refers to a collection of isolated cellulose microfibrils (nanofibers) or microfibril bundles derived from cellulose raw material.

Also cellulose whiskers (nanowhiskers, cellulose nanocrystals, cellulose nanorods, rod-like cellulose microcrystals or cellulose nanowires) may be used in the present invention.

The term "nanofibrillated cellulose" refers to a collection of isolated cellulose microfibrils (nanofibers) or microfibril bundles derived from cellulose raw material. Microfibrils have typically high aspect ratio: the length exceeds one micrometer while the number-average diameter is typically below 200 nm. The diameter of microfibril bundles can also be larger but generally less than 1 μm. The smallest microfibrils are similar to so called elementary fibrils, which are typically 2-12 nm in diameter. The dimensions of the fibrils or fibril bundles are dependent on raw material and disintegration method.

NFC is characterized by very high water retention values, a high degree of chemical accessibility and the ability to form stable gels in water or other polar solvents. NFC product is typically a dense network of highly fibrillated celluloses. NFC may also contain some hemicelluloses; the amount is dependent on the plant source.

To obtain NFC mechanical disintegration of cellulose pulp, oxidized cellulose raw material or microbial cellulose is carried out with suitable equipment such as a refiner, grinder, homogenizer, colloider, friction grinder, ultrasound-sonicator, fluidizer such as microfluidizer, macrofluidizer or fluidizer-type homogenizer. Preferably mechanically disintegrated NFC is used.

Several different grades of NFC have been developed using various production techniques. The grades have different properties depending on the manufacturing method, degree of fibrillation and chemical composition. The chemical compositions of the grades also vary. Depending on the raw material source, e.g. HW vs. SW pulp, different polysaccharide composition exists in the final NFC product. Typically, non-ionic or native or neutral grades have wider fibril diameter while the chemically modified grades are a lot thinner. Size distribution is also narrower for the modified grades.

The term "nanofibrillated cellulose" refers here to one grade of NFC or a combination of two or more different grades of NFC. For example modified grades of fibril cellulose may be blended with native grade for enhancing binding of certain compounds to the gel.

NFC is understood to encompass here also any chemically or physically modified derivates of cellulose nanofibers or nanofiber bundles, obtained from any cellulose raw materials. The chemical modification of cellulose may be based for example on carboxymethylation, oxidation, (TEMPO-oxidation), esterification, or etherification reaction of cellulose molecules, whereby cationic and anionic grades of NFC are obtained. Modification may also be realized by physical adsorption of anionic, cationic, or non-ionic substances or any combination of these on cellulose surface. TEMPO-oxidation refers to N-oxyl mediated oxidation (e.g. 2,2,6,6-tetra methyl-1-piperidineN-oxide), which leads to very labile cellulose material, which is easy to disintegrate to microfibrillar cellulose. The described modifications can be carried out before, after, or during the production of cellulose nanofibers. Certain modifications may lead to materials that are degradable in human body. Modified grades are typically prepared from bleached pulps. In the modified grades, the hemicelluloses are also modified together with the cellulose domain. Chemically modified grades, such as anionic and cationic grades typically have their surface charge modified. Thus a suitable NFC or a combination of different NFC grades may be selected and designed. Most probably, the modification is not homogeneous, i.e. some parts are more modified than others. Thus, detailed chemical analysis is not possible—the modified products are always complicated mixtures of different polysaccharide structures.

Dry powders of NFC may conveniently be manufactured by spray drying and/or lyophilization of suspension or dispersions containing said fibril cellulose, using any conventional methods known in the art.

The NFC gel or hydrogel refers here to a dispersion of nanofibrillated cellulose. The nanofibrillated cellulose has excellent gelling ability, which means that it forms a hydrogel already at a low consistency in polar, suitably an aqueous medium.

Suitably the cellulose raw material such as cellulose pulp is pretreated with acid and base prior to the mechanical disintegration. The pretreatment is effected by subjecting the cellulose pulp to acid treatment, preferably with hydrochloric acid for removing any positively charged ions having a charge more than +1, followed by treatment with an inorganic base containing positively charged ions having a charge +1, preferably NaOH, where $Na^+$ ions replace the earlier ions. The absence of any positively charged ions having a charge more than +1 is particularly advantageous in life science and molecular biology applications where complex formation of DNA with ions with charges more than +1 can be avoided. The pretreatment provides the final product excellent gelling properties and transparency. The pretreated NFC product is referred here to as ion exchanged NFC. According to one preferable embodiment, in exchanged NFC is used, suitably native ion exchanged NFC.

Microbial purity of NFC is often essential. Therefore, NFC may be sterilized, prior to use, suitably in a gel form. For example autoclave may suitably be used in said sterilization. In addition, it is important to minimize the microbial contamination of the product before and during the mechanical disintegration, such as fibrillation. Prior to fibrillation/mechanical disintegration, it is advantageous to aseptically collect the cellulose pulp from the pulp mill immediately after bleaching stage when the pulp is still sterile.

Because of the many unique properties of NFC, it is particularly suitable as a matrix material for sustained delivery of bioactive agents. It is non-toxic and bio-stabile, i.e. it forms a uniform matrix which does not fragment, and it does not swell in a similar way as other hydrogels usually do. The matrix structure is simple, is applicable even without any supporting membrane, and can be formulated in different shapes, for example as a sandwich type matrix. NFC matrices are compatible and suitable for a large range of bioactive agents and materials and thus they can be incorporated in a vide range of materials used in devices designed for the delivery of bioactive agents.

Matrix

The matrix comprises at least one grade of NFC, at least one bioactive agent and optionally at least one pharmaceutically acceptable polar solvent and optional additives.

Suitably the NFC is selected from native nanofibrillated celluloses and anionic nanofibrillated celluloses and any combinations thereof. Preferably the NFC is native nanofibrillated cellulose. Preferably plant derived NFC is used.

NFC provides controlled swelling of the hydrogel where the swelling takes place preferably only in one dimension. In matrices for use in devices the swelling ranges typically between 0 and 10%. Suitably the native (non-ionic) grades provide desired swelling characteristics and they are particularly suitable for providing sustained delivery of bioactive agents.

Suitably the polar solvent is water, another pharmaceutically acceptable polar solvent, such as ethanol, or a combination thereof.

The amount of NFC in the matrix ranges from 0.1 to 99.9 wt %. The matrix may be essentially dry whereby it may contain from 0.01 up to 10 wt % of water, suitably from 0.1 to 10 wt %.

The matrix may also be semi-dry or hydrogel, which contains typically 0.2 to 80 wt % NFC and from 10 to 80 wt % of water.

The matrix may comprise from 0.01 to 80 wt % of water. The water content varies depending on the dosage form and site of administration.

The amount of the bioactive agent incorporated or loaded in the matrix varies depending on the particular bioactive agent, the desired therapeutic effect and the time for which the system is expected to provide therapy. The matrix may be used as a reservoir of the bioactive agent. Reservoirs with varying sizes and shapes can be formulated for administering dosages for different therapeutical areas. The composition of the matrix is varied depending on the type of the formulation, bioactive agent, therapeutic effect, desired treatment time.

The upper limit on the amount of bioactive agent depends on the size of the reservoir. The lower limit depends on the activity of the bioactive agent and on the expected release time. A person skilled in the art is readily able to determine the amount of the bioactive agent needed for each specific application of the delivery system. Suitably, the amount of the bioactive agent varies between 0.0001 to 70 wt %, calculated from the total dry weight of the matrix. When it is mixed into the matrix, the preferred amount being between 0.001-50 wt %. Other possible ranges of the amount of the bioactive agent are 0.5-60 wt %, 5-55 wt %, 10-50 wt %, 25-60 wt %, 40-50 wt % and 15-35 wt %. The matrix may comprise one bioactive agent or a combination of at least two active agents.

The pH of the matrix is adjusted according to the site of use with pharmaceutically acceptable agents used generally for pH adjustments, suitably pharmaceutically acceptable buffers may be used and they are selected depending on the site of application. For example, in products designed for use as implants, or intrauterine or ocular use, the pH may be adjusted to approx. 7, and for products designed for vaginal use the pH may be adjusted to approx. 5.

The matrix may further comprise additives. Examples of said additives are agents for controlling swelling, agents for controlling hydrophobicity, thickening agents, polymeric substances, pharmaceutically acceptable solvents, antioxidants, stabilizators and preservatives etc.

The release rate of the bioactive agent may be controlled by varying the particle size of the bioactive agent in case of hydrophobic substances, by varying the thickness of the matrix, by the selection of the NFC, by selection of additives and by varying the process parameters used in the manufacture, etc.

The particle size of the bioactive agent is suitably from 1 nm to 1000 μm, preferably from 10 nm to 500 μm, particularly preferably from 10 nm to 100 μm.

The thickness of the matrix may be varied depending on the dosage form, the desired therapeutic effect and the time for which the system is expected to provide therapy. Examples of some thicknesses of matrices are from 1 to 1000 μm, from 5 to 500 μm, and 50 to 300 μm.

The matrix may also comprise a cellulolytic enzyme providing enzymatic degradation of NFC cellulose molecules.

Bioactive Agent

The bioactive agent is a therapeutically active agent or a prophylactic agent, or any combination thereof.

Suitably the bioactive agents include, but are not limited to, the following: hormones, steroids, contraceptive drugs, drugs for hormone replacement therapy, antiandrogens, selective androgen receptor modulators (SARM), drugs for the treatment of premenstrual syndrome, drugs for the treatment of endometriosis, prostaglandin synthesis inhibitors, progestins, drugs for the treatment of uterine fibroids (uterine leiomyomata and leiomyosarcoma), drugs for cervical ripening/induction of labour, selective estrogen receptor modulators (SERMs), selective progestin receptor modulators (SPRM), antimalarial substances, osteoporosis drugs, antiprogestins, aromatase inhibitors, bone active substances, anti-urinary incontinence substances, serotonin reuptake inhibitors (SSRIs), drugs for genito-urinary disorders, antiemetic drugs, 5HT3 antagonists, anti-angiogenesis factors, growth factors, enzymes, anesthetics, analgesics, anticoagulants and thrombolytic substances, anti-inflammatory substances, antimicrobials, anti-protozoal substances, antiviral substances, neuroleptic and antipsychotic drugs, opiate antagonists and agonists, anti-fibroid substances, antihypertensives, antiarrhyrthmics, angiotensin inhibitors, anti-protozoal substances, anti-addiction drugs, anti-angiogenesis factors, anti-bacterial substances, anticancer chemotherapeutic substances, antifungals, antioxidants, diuretics, drugs for the central nervous system, fibrinolytic substances, free radical scavengers, gene therapy substances, growth factors, neurotrophic factors, peptides, photodynamic therapy substances, proteins, symphatomimetic substances, thrombin inhibitors, thrombolytic substances, beta-adrenergic blocking agents, cardiotonic glycosides, adrenergic stimulants, vasodilators, antimigraine preparations, anticoagulants and thrombolytic agents, hemostatic agents, analgesics and antipyretics, neurotoxins, neuroleptics, bacteriostatics, sedatives, antianxiety agents, antipsychotic drugs, antidepressants, anti-Alzheimer's agents, anti-Parkinson's agents, anticonvulsants, antiemetics and antinauseants, antirheumatoid agents, muscle relaxants, corticosteroids, pituitary hormones and their active derivatives or analogs, hypoglycemic agents, thyroid hormones, ovulation inducers; diuretics, antidiuretics; prostaglandins and any combination of at least two thereof.

Suitably the substances suppressing endometrial bleeding include, but are not limited to prostaglandin synthesis inhibitors like diclofenac sodium, NSAIDs, such as naproxen, indomethacin, ibuprofen, mefenamic acid, flurbiprofen, inhibitors of leukotriene, e.g. zafirlukast and montelukast and its salts, oxytocin antagonists, pancreatic trypsin inhibitors like Trasylol, COX-inhibitors, antifibrinolytic drugs, such as tranexamic acid and precursors thereof, aminocapronic acid, PAI-1, desmopressin, clomiphene citrate, p-aminomethyl-benzoic acid, estrogens, antiestrogens, aromatase inhibitors, cytokine inhibitors, glucocorticoids, progestogens with pronounced glucocorticoid acticity, danazol and gestrinone.

The terms "progestational steroid" and "progestin" are used interchangeably to refer to an agent, natural or synthetic, that affects some or all of the biological changes produced by progesterone, which is a hormone of the corpus luteum.

Therapeutically active substances especially suitable for use in the present invention include gestagenes selected from the group of levonorgestrel, norgestimate, norethisteron, Desogestrel dydrogesterone, drospirenone, 3-beta-hydroxydesogestrel, 3-ketodesogestrel (=etonogestrel), 17-deacetylnorgestimate, 19-norprogesterone, acetoxypregnenolon, allylestrenol, amgeston, chlormadinone, cyproterone, demegestone, desogestrel, dienogest, dihydrogesteron, dimethisterone, ethisteron, ethynodiol diacetate, flurogestonacetate, gastrinon, gestodene, gestrinon, hydroxymethylprogesteron, hydroxyprogesterone, lynestrenol (=lynoestrenol), medrogeston, medroxyprogesterone, megestrol, melengestrol, nomegestrol, norethindron (=norethisteron), Norelgestromin) norethinodrel, norgestrel (including d-norgestrel and dl-norgestrel), norgestrienon, normethisteron, progesteron, quingestanol, (17alpha)-17-hydroxy-11-methylen-19-norpregna-4,15-dien-20-yn-3-on, tibolon, trimegestone, algeston acetophenid, nestoron, promegeston, 17-hydroxyprogesteronester, 19-nor-17hydroxyprogesteron, 17alpha-ethinyl-testosteron, 17alpha-ethinyl-19-nor-testosteron, d-17beta-acetoxy-13beta-ethyl-17alpha-ethinyl-gon-4-en-3-onoxim, tanaproget, tibolone, nestorone, 17-hydroxy progesterone derivatives, 19-nor-testosterone derivatives, 19-nor-progesterone derivatives, fuingestanol acetate, dimethiderome, phytoprogestins, animal-derived progestins, and metabolic derivatives of animal-derived progestins, 17-alpha.-acetoxy-13.beta.-ethyl-17.alpha.-ethinyl-gon-4-en-3-one oxime, gestonorone caproate, promegestone,13β-ethyl-17β-hydroxygon-4-en-3-one, 13β,17α-diethyl-17β-hydroxygon-4-en-3-one, and 17α-ethinyl-β-acetoxy-19-norandrost-4-en-3 one oxime.

Therapeutically active substances especially suitable for use in the present invention include contraceptive drugs selected from the comprising Mestranol, Nonoxynol-9, ST-1435 (a progestin), Pain end Migraine 5HT-1 receptor blockers such as Almotriptan, Eletriptan, Frovatriptan, Naratriptan, Rizatriptan, Sumatriptan, and Zolmatriptan.

Therapeutically active drugs for hormone replacement therapy, especially suitable for use in the present invention include Luteinizing Hormone Releasing Hormone, ST-1435.

The terms "estrogenic steroid" and "estrogen" are used interchangeably to refer to an agent, natural or synthetic, that exerts biological effects characteristic of estrogenic hormones such as estradiol. As used herein, the terms "estrogenic steroid" and "estrogen" also encompasses "conjugated estrogens," which are an amorphous preparation of naturally occurring, water-soluble, conjugated forms of mixed estrogens that typically are obtained from the urine of pregnant mares (e.g., sodium estrone sulfate). Also included are "esterified estrogens," which are a mixture of the sodium salts of sulfate esters or glucanoride of sulfate conjugates of estrogenic substances.

Examples of suitable estrogens include, without limitation, estradiol, estradiol valerate, estradiol benzoate, 17-βestradiol, estradiol cypionate, estrone, piperazine estrone sulfate, estriol, ethyl estradiol, estradiol hemihydrate, polyestradiol phosphate, estrone potassium sulfate, estetrol, benzestrol, chlorotrianisene, methallenestril, dienestrol, diethylstilbestrol diphosphate, mestranol, diethylstilbestrol (DES), quinestranol, phytoestrogens, 1,3,5(10)-estratriene-3,17α-diol dipropionate, estra-1,3,5(10)-triene 3,17-.alpha.-diol valerate, 17-ethynyl estradiol-3-methyl ether, 17-ethinyl estradiol-3-cyclopentylether, animal-derived estrogens (e.g., conjugated equine estrogens), and metabolic derivatives of animal-derived estrogens. These also include any steroid or non-steroidal compound that binds either to the known estrogen receptors that exist within cells or to estrogen receptors that bind to extracellular membranes and cause biologic effects that mimic those of estradiol or other estrogenic compounds, or esters, pseudopolymorphs, pharmaceutically acceptable solvates, hydrates or hemihydrates thereof.

Examples of suitable androgens include, without limitation, testosterone, methyltestosterone, fluoxymesterone, testosterone acetate, testosterone cypionate, testosterone enanthate, testosterone propionate, oxymetholone, ethylestrenol, oxandrolone, nandrolone phenpropionate, nandrolone decanoate, testosterone buccilate, stanozolol, dromostanolone propionate, androstenedione, dehydropepiandrosterone, dehydroepiandrosterone sulfate (DHEAS), dihydrotestosterone, phytoandrogens, animal-derived androgens, and metabolic derivatives of animal-derived androgens. This also included any steroidal or non-steroidal compounds that bind to either the cytoplasmic or membrane bound androgen receptor and produce biologic effects that mimic testosterone or other androgenic compounds. Closely related androgenic compounds which are synthetically derivatized from testosterone known to provide the same or a similar physiologic activity include testosterone salts and esters, cyproterone acetate, danazol, finasteride, fluoxymesterone, methyltestosterone, nandrolone decanoate, nandrolone phenpropionate, oxandrolone, oxymetholone, stanozolol, and testolactone.

A "selective androgen receptor modulator" ("SARM") is a compound that is an androgen analog and which exerts tissue-selective effects. Such compounds can function as androgen antagonists or partial agonists. Examples of suitable SARM:s include cyproterone acetate, hydroxyflutamide, bicalutamide, spironolactone, 4-(trifluoromethyl)-2 (1H)-pyrrolidino[3,2-g]quinolinone derivatives, 1,2-dihydropyridono[5,6-g]quinoline derivatives, and piperidino[3,2-g]quinolinone derivatives.

A "selective estrogen receptor modulator" ("SERM") is a compound that is an estrogen analog and which exerts tissue-selective effects. Such compounds can function as estrogen antagonists or partial agonists. Examples of suitable SERM:s include tamoxifen, raloxifene, clomiphene, droloxifene, idoxifene, toremifene, bazedoxifen, arzoxifen, lasofoxifen, ormeloxifene, levormeloxifene, toremifene, 4-hydroxy-tamoxifen, 4-hydroxy-toremifene, ospemifene, tibolone, ICI 182,780, ICI 164,384, diethylstilbesterol, genistein, nafoxidine, moxestrol, 19-nor-progesterone derivatives, and 19-nor-testosterone derivatives.

A "selective progestin receptor modulator" ("SPRM") is a compound that is an progesterone analog and which exerts tissue-selective effects. Such compounds can function as progesterone antagonists or partial agonists. Examples of suitable SPRMs include RU486 (mifepristone), CDB2914 (ulipristal, ulipristal acetate), 19-nor-progesterone derivatives, 19-nor-testosterone derivatives, 6-aryl-1,2-dihydro-2,2,4-trimethylquinoline derivatives, 5-aryl-1,2-dihydro-5H-chromeno[3,4-f]quinoline derivatives, 5-alkyl 1,2-dihydrochomeno[3,4-f]quinoline derivatives, and 6-thiophenehydroquinoline derivatives.

Examples of suitable antiandrogens include cyproterone acetate, flutamide, nilutamide and danazol.

Examples of suitable aromatase inhibitors include but are not limited to exemestane, formestane, and atamestane, and the like. Suitable examples of non-steroidal aromatase inhibitors include but are not limited to fadrozole, letrozole, vorozole, anastrozole, finrozole, and tamoxifen.

Examples of suitable antiprogestins include but are not limited to the following:

11beta-[(4-(Dimethylamino)phenyl]-17beta-hydroxy-17alpha-(1-propinyl)-4,9-estradien-3-one (mifepristone)
11beta-[(4-(Dimethylamino)phenyl]-17beta-hydroxy-17alpha-(1-propinyl)-18-homoestra-4,9-dien-3-one
11beta-[(4-(Dimethylamino)phenyl]-17beta-hydroxy-17alpha-(1-propinyl)-17a-homoestra-4,9,16-trien-3-one
11beta-[(4-Dimethylamino)phenyl]-17alpha-hydroxy-17beta-(3-hydroxypropyl)-13α-methyl-estra-4,9-dien-3-one (onapristone)
(Z)-11beta-[(4-dimethylamino)phenyl)]-17beta-hydroxy-17alpha-(3-hydroxy-1-propenyl)estra-4,9-dien-3-one (lilopristone)
11beta-(4-Acetylphenyl)-17beta-hydroxy-17alpha-(1-propinyl)estra-4,9-dien-3-one
(Z)-11beta-(4-acetylphenyl)-17beta-hydroxy-17alpha-(3-hydroxy-1-propenyl)estra-4,9-dien-3-one
11beta-(4-Methoxyphenyl)-17beta-hydroxy-17alpha-ethynyl-4,9-estradien-3-one
(Z)-11beta-[(4-Dimethylamino)phenyl)]-17beta-hydroxy-17alpha-(3-hydroxy-1-propenyl)estr-4-en-3-one
4-[17β-Methoxy-17α-(methoxymethyl)-3-oxoestra-4,9-dien-11β-yl]benzaldehyde-1-(E]-oxime
4-[17β-Hydroxy-17α-(methoxymethyl)-3-oxoestra-4,9-dien-11β-y]benzaldehyde-1-(E)-oxime
4-[17β-Methoxy-17α-(methoxymethyl)-3-oxoestra-4,9-dien-11β-yl]benzaldehyde-1-(E)-[O-(ethylamino)carbonyl]oxime,
4-[17β-Methoxy-17α-(methoxymethyl)-3-oxoestra-4,9-dien-11β-yl]benzaldehyde-1-(E)-[O-(ethoxy)carbonyl]oxime
4-[17β-Methoxy-17α-(methoxymethyl)-3-oxoestra-4,9-dien-11β-yl]benzaldehyde-1-(E)-[O-(ethylthio)carbonyl]oxime
4-[17β-Methoxy-17α-(ethoxymethyl)-3-oxoestra-4,9-dien-11β-yl]benzaldehyde-1-(E)-[O-(ethylthio)carbonyl]oxime
4-[17β-Hydroxy-17α-(methoxymethyl)-3-oxoestra-4,9-dien-11β-yl]benzaldehyde-1-(E)-[O-(n-propylthio)carbonyl]oxime
(Z)-6'-(4-cyanophenyl)-9,11α-dihydro-17beta-hydroxy-17α-[4-(1-oxo-3-methylbutoxy)-1-butenyl]4'H-naphtho[3',2',1'; 10,9,11]estr-4-en-3-one
(Z)-6'-(4-cyanophenyl)-9,11α-dihydro-17beta-hydroxy-17α-[3-(1-oxo-3-methylbutoxy)-1-propenyl]4'H-naphtho[3',2',1';10,9,11]estra-4,15-dien-3-one
(Z)-6'-(4-cyanophenyl)-9,11α-dihydro-17beta-hydroxy-17α-(3-hydroxy-1-propenyl)-4'H-naphtho[3',2',1':10,9,11]estra-4,15-dien-3-one
(Z)-6'-(3-pyridinyl)-9,11α-dihydro-17beta-hydroxy-17α-(3-hydroxy-1-propenyl)-4'H-naphtho[3',2',1':10,9,11]estra-4,15-dien-3-one
11β-(4-acetylphenyl)-17β-hydroxy-17α-(1,1,2,2,2-pentafluoroethyl)estra-4,9-dien-3-one
6'-(Acetyloxy)-9,11α-dihydro-17β-hydroxy-17α-(1,1,2,2,2-pentafluoroethyl)-4'H-naphth[3',2',1':10,9,11]estr-4-en-3-one
9,11α-Dihydro-17β-hydroxy-6'-(hydroxymethyl)-17α-(1,1,2,2,2-pentafluoroethyl)-4'H-naphth[3',2',1':10,9,11]estr-4-en-3-one
11beta-(4-Acetylphenyl)-19,24-dinor-17,23-epoxy-17alpha-chola-4,9,20-trien-3-one
11beta-(4-Methoxyphenyl)-19,24-dinor-17,23-epoxy-17alpha-chola-4,9,20-trien-3-one
(Z)-11beta,19-[4-(3-Pyridinyl)-o-phenylene)-17beta-hydroxy-17α-[3-hydroxy-1-propenyl]-4-androsten-3-one,
(Z)-11beta,19-[4-(4-Cyanophenyl-o-phenylene)]-17beta-hydroxy-17α-[3-hydroxy-1-propenyl]-4-androsten-3-one
11beta-[4-(1-methylethenyl)phenyl]-17α-hydroxy-17beta-(3-hydroxypropyl)-13α-estra-4,9-dien-3-one
11beta-[4-(3-Furanyl)phenyl]-17α-hydroxy-17beta-(3-hydroxypropyl)-13α-estra-4,9-dien-3-one
4',5'-Dihydro-11beta-[4-(dimethylamino)phenyl]-6beta-methylspiro[estra-4,9-dien-17beta,2'(3'H)-furan]-3-one
4',5'-Dihydro-11beta-[4-(dimethylamino)phenyl]-7beta-methylspiro[estra-4,9-dien-17beta,2'(3'H)-furan]-3-one
4-beta,17α-Dimethyl-17beta-hydroxy-3-oxo-4α,5-epoxy-5α-andros tan-2α-carbonitrile
7α-[9-(4,4,5,5,5-Pentafluoropentyl)sulfinyl]nonyl]estra-1,3,5(10)-trien-3,17beta-diol
3-(4-chloro-3-trifluoromethylphenyl)-1-(4-iodobenzenesulphonyl)-1,4,5,6-tetrahydropyridazine; (R,S)3-(4-chloro-3-trifluoromethylphenyl)-1-(4-iodobenzenesulphonyl)-6-methyl-1,4,5,6-tetrahydropyridazine
3-(3,4-dichlorophenyl)-1-(3,5-dichlorobenzoyl)-1,4,5,6-tetrahydropyridazine
3-(3,4-dichlorophenyl)-1-(2,5-dichlorobenzenesulphonyl)-1,4,5,6-tetrahydropyridazine
7,8-Dibromo-3,4-diazo-1,2,3,10,10a-hexahydro-3-(4-iodobenzenesulphonyl)-phenanthrene
7-Chloro-3,4-diazo-1,2,3,9,10,10a-hexahydro-3-(2,5-dichlorobenzenesulphonyl)-phenanthrene Bioactive agents particularly suitable for transdermal delivery are typically relatively small compounds having a molecular weight less than 1000 Da, have suitable lipid and water solubility, and are electrically uncharged. Further said agents have strong first-pass metabolism and liver toxicity and they are inconvenient for per os or i.v. administration. Additionally, in transdermal delivery the therapeutic dose of the agent should be small, daily dose at most 10 mg and effective plasma concentration at most 5 ng/ml, and the compound should cause no sensitization, irritation or allergies. Examples of suitable bioactive agents for transdermal use include but are not limited to the following: scopolamine, nitroglycerin, nicotine, clonidine, lidocaine, fentanyl, estradiol and other female hormones, testosterone and other male hormones, norelgestromin, ethinyl estradiol, diclofenac, oxydutynin, rotigone, methylphenidate, and rivastigmine.

Bioactive peptides and proteins may also be incorporated in the matrix of the present invention. Examples of suitable peptides include but are not limited to growth hormone release factor, gonadotropin releasing hormone agonists, LHRH, leuprolide, buserelin, nafarelin, vasopressin, arginine vasopressin, desmopressin, 8-arginine vasopressin desglycinamide, somatostatin analogs, octreotide, cholecystokinin analogs, CCK-8, angiotensin 2, calcitonins, parathyroid hormone, and insulin.

The matrix for sustained delivery of bioactive agents, according to the invention may be used for intraoral (e.g. sub-lingual), topical, ocular, intraocular, transdermal, intestinal, rectal, subcutaneous, vaginal and intrauterine administrations. The NFC matrix is also especially suitable for parenteral and mucoadhesive applications.

The matrix for sustained delivery of bioactive agents, according to the invention may be used as such, incorporated in dosage forms, in transdermal patches, in medical devices, implants and the like.

Manufacture of the Matrix

The matrix according to the invention may be manufactured according to any one of the following methods A-D, whereby NFC membranes or matrices comprising particles or molecules of the bioactive agent(s) are obtained:

A: Blending, followed by removal of water and drying
B. Spray-drying method
C. Extrusion method
D. Impregnation method A. The first alternative method comprises the steps where at least one bioactive agent is blended with an aqueous suspension or dispersion, suitably gel containing 0.01-50 wt % of nanofibrillated cellulose to obtain a mixture, followed by removal of water from the mixture and drying. When the aqueous gel contains 0.01-10 wt %, preferably 0.1-2 wt % of nanofibrillated cellulose, the removal of water from the mixture is suitably carried out by filtration (either vacuum or pressure filtration) using filter pore size from 100 nm to 50 µm or evaporation. When the aqueous gel contains 5-50 wt %, preferably 10-30 wt % of nanofibrillated cellulose the removal of water from the mixture is suitably carried out by compressing using suitably a hydraulic press. Ultrasound sonication may be used in the blending. The drying of the remaining wet matrix is carried out at a temperature from 0 to 250° C., as air-drying, in an oven etc. The water used in the gel is preferably sterilized water of high purity. The porosity of the matrix can be altered by using pharmaceutically acceptable water miscible solvents with water during the blending, filtration, or drying stages.

Mixing of a bioactive agent with a NFC suspension or gel is an important step for even distribution of the agent within the matrix and for breaking possible particle agglomerates. A mild mechanical mixing is suitably applied, optionally followed by sonication that assists in breaking the particle agglomerates and facilitates even distribution of the agent within the suspension. Upon drying of NFC hydrogel, nanofibers start to aggregate and form tight bonds between each other; hydrogen bonds between water molecules and nanofibers are replaced by hydrogen bonds between the nanofibers. This process is known as hornification in the literature and its known to produce high-strength materials without the use of binders (Young, Cellulose 1, 107-130, 1994; Hult et al. Polymer 42:3309-3314, 2001, Fernandez Diniz et al. Wood Sci Technol 37, 489-494, 2004). Hornification is irreversible, i.e. the original water-swollen state is not regained even if the fibres are resuspended in water. In this way, a tight fiber network is formed entrapping the solid drug particles. This manufacturing method results in the production of film-like matrix systems.

The advantage of this production method is its flexibility for possible variations depending on the desirable properties of the final product as well as on the properties of the drug used. Thus the matrix thickness can be easily tailored by changing the concentration of NFC suspension. Higher concentrations will result in the production of thicker matrices. Furthermore, the drying step can be adjusted to suit thermo-sensitive drugs. The NFC films can be produced by drying at room temperature as well.

Compared to the manufacture of many polymer matrices currently used in drug delivery systems, this method for manufacturing the matrix or the delivery system by using NFC is simple, because no catalysts are needed and relatively low temperatures can be used which is important when biomolecules, such as peptides, proteins and the like are used as active substances. Dissolution rates can be adjusted for example by modifying the drug load of the bioactive agent in the matrix.

The advantage of this production method is its flexibility for possible variations depending on the desirable properties of the final product as well as on the properties of the bioactive agent used. Thus the matrix thickness may be easily tailored by changing the concentration of NFC suspension. Higher concentrations will result in the production of thicker matrices. Furthermore, the drying step may be adjusted to suit thermo-sensitive agents.

B. The second alternative method comprises the steps where at least one bioactive agent is dissolved in a solvent or buffer solution to obtain a solution containing 0.01-80% of the dissolved agent, the solution is then blended with an aqueous suspension or dispersion, suitably gel containing 0.1-5%, preferably 0.5-1.6% of nanofibrillated cellulose to obtain a suspension or mixture containing from 0.05-10%, preferably 0.1-2% of nanofibrillated cellulose and 0.01-5%, preferably 0.01-2% of the agent, and the suspension is then dried in a spray drier. Suitably ultrasound sonication is used in the blending step. Suitably the spray drier is equipped with a two-fluid nozzle. Suitably it is operated in co-current mode. Suitably the inlet temperature is from 180-230° C. and the outlet temperature is from 80-140° C. The matrix is obtained as a powdery product which can be incorporated in a sustained release formulation, medical device, transdermal patch etc.

C. The third alternative method comprises the steps where an aqueous suspension or dispersion, suitably gel containing 0.1-50%, preferably 1-10% of nanofibrillated cellulose and at least one bioactive agent is introduced into a volume of organic extraction agent miscible with water into the form of one or several elements, preferably elongated elements, removing the elements and drying them. Suitably the aqueous gel is introduced to the extraction agent through a port, such as a slit or nozzle or as larger blocks which are crumbled into smaller entities by agitation. Suitably the elements are washed with the organic extraction agent prior drying. The element remains in this method coherent and it does not become dispersed.

D. The fourth alternative method comprises the steps where an aqueous gel containing 0.1-50%, preferably 1-10% of nanofibrillated cellulose is introduced into a volume of organic extraction agent miscible with water and containing at least one bioactive agent, into the form of one or several elements, preferably elongated elements, removing the elements and drying them. Suitably the aqueous gel is introduced to the extraction agent through a port, such as a slit or nozzle or as larger blocks which are crumbled into smaller entities by agitation. Suitably the elements may be washed with the organic extraction agent prior drying. In this method the NFC gel is impregnated with the bioactive agent. This method is particularly suitable for bioactive agent having limited water solubility.

Water can be extracted from NFC gels using a pharmaceutically acceptable water-miscible liquid, e.g. ethanol as an extraction agent by a practical method which reduces the drying time and makes it possible to manufacture a variety of products starting from the NFC hydrogel.

Simultaneously with drying, a NFC product may be obtained which is in the form of fiber or film, which may contain one or more other constituents mixed with the nanocellulose fibrils therein. These constituents are incorporated into the hydrogel, in which case they remain in the fiber or film during the formation, or inside the extraction agent, in which case they will penetrate into the fiber or film while the fiber or film is in contact with the extraction agent. Both alternatives are possible at the same time when the fiber or film is prepared.

NFC hydrogel is introduced into a water-miscible liquid (extraction agent) so that it exists within the extraction agent as discrete physical entities. If a fiber product is to be manufactured from the NFC hydrogel, the hydrogel is introduced into the extraction agent initially as continuous elongated "thread"-like objects, either as one individual thread or two or more threads in parallel.

Alternatively, the hydrogel can be introduced in the water-miscible extraction agent as continuous, wider 2-dimensional object for manufacturing a NFC-product in the form of a film, which has preferably constant thickness.

The water in the NFC hydrogels can be completely or partly changed to e.g. ethanol. In the second stage of the process, the extraction agent is removed for example in vacuum and/or elevated temperature (elevated temperature, if used, is a temperature higher than 25° C.), and essentially dry NFC is obtained. The drying can take place also by pressure filtration.

Possible ways of introducing the hydrogel into the extraction agent volume to create discrete physical entities include supply through a port, for example through nozzles or a slit, or directly into the extraction agent in larger blocks which are crumbled into smaller entities in the extraction agent volume by agitating.

The organic extraction agent is any liquid that is miscible with water and preferably has moderate polarity. Suitable extraction agents are organic liquids, preferably water-miscible alcohols including but not limited to methanol, ethanol, and isopropanol, as well as dioxane and THF.

The bioactive compound can be added either to the NFC hydrogel or to the extraction agent, depending on their characteristics.

In industrial scale, the NFC gel is introduced into the extraction bath through a suitable port that allows the formation of discrete physical entities whose shape is determined by the port and the rate of introduction of the gel. The port may comprise several orifices through which the NFC hydrogel is extruded. The hydrogel can be introduced for example through an extruder with a suitable breaker plate that generates numerous elongate entities, hydrogel "worms" or ribbons, in general thread-like elongate objects in the extraction bath. Alternatively, a spray nozzle could be used if the aim is to obtain small spheres or beads, in which case the hydrogel is introduced at short intervals, "dropwise", rather than as continuous strand. A port introducing the hydrogel in this way can comprise several spray nozzles in parallel from which the hydrogel issues as drops.

The concentration of the NFC fibrils in the gel is preferably but not limited to 0.5-5%, based on the total weight of the gel.

One or more desired additives may be incorporated in the matrix during the manufacture, suitably by blending the additive in the hydrogel.

Support Material

The matrix may be incorporated in final formulations for sustained delivery of bioactive agents, such as transdermal patches, which may be designed for sustained release from 24 hours to one week, in medical devices including intraocular devices, medical implants, gynaecological implants, intrauterine delivery systems and vaginal delivery systems, for providing sustained release between 1 month up to 10 years, typically from 1 to 5 years, as well as vaginal delivery systems with sustained release from 1 month to 28 months, typically from 2 weeks to 1 month. The matrix according to the invention may also be incorporated in final formulations suitable for use in oral (e.g. sub-lingual), topical, intraocular, intestinal, rectal, and subcutaneous administrations, as well as for parenteral and mucoadhesive applications.

Suitable support materials are naturally occurring or synthetic materials, preferably materials that are biologically compatible with body fluids and tissues occurring in human body, and essentially insoluble in body fluids with which the device will come in contact. The use of rapidly dissolving materials or materials highly soluble in natural body fluids is to be avoided since the system is aimed to remain in place for prolonged periods of time. Suitably naturally occurring polymers and biomolecules as well as various synthetic polymers can be used.

Examples of suitable support materials to be used in combination with the mentioned NFC matrix but are not limited to, comprise polysiloxanes, poly (dimethyl siloxane) (PDMS), copolymers of dimethylsiloxanes, methylvinylsiloxanes, polyolefins such as polyethylene, polypropylene, and polybutylenes; polyolefin copolymers, e.g., ethylenic copolymers such as ethylene vinyl acetate (EVA) copolymers, ethylene-methacrylic acid copolymers and ethylene-acrylic acid copolymers, ethylene/propylene copolymers, acrylic acid polymers, ethylene/ethyl acrylate copolymers, poly(butylmethacrylate), plasticized poly(ethylene terephthalate), cross-linked poly(vinyl-pyrrolidone), thermoplastic polyurethanes and thermoplastic polyurethane elastomers including polyurethane copolymers, for example such as block and random copolymers that are polyether based, polyester based, polycarbonate based, aliphatic based, aromatic based and mixtures thereof; silicone containing thermoplastic polyurethanes, polycarbonates; polyurethanepolyureas, polyisocyanurates, polyurethane-polyisocyanurates, polyimide-polyurethanes, poly(isobutylene), polybutadiene, polyisoprene, poly(methacrylate), polymethyl methacrylate, polyalkylcyanoacrylate, vinylidene chloride acrylonitrile, vinyl chloride diethyl fumarate, vinyl aromatic polymers such as polystyrene; styrene-isobutylene-styrene copolymers, vinyl aromatic copolymers such as copolymers of olefins and styrene or alpha-methyl styrene, for example, butadiene-styrene copolymers and copolymers of polyisobutylene with polystyrene or polymethylstyrene, for example, polystyrene-polyisobutylene-polystyrene triblock copolymers, poly(hydroxyethylmethacrylate) (pHEMA), polyacetals; chloropolymers such as polyvinyl chloride (PVC); fluoropolymers such as polytetrafluoroethylene (PTFE); polyesters such as polyethyleneterephthalate (PET); polyester-ethers; polyamides such as nylon, plasticized nylon and plasticized soft nylon; polyamide ethers such as polyether block amides (PEBA) comprising nylon blocks, polyvinyl acetate, polyacrylonitriles, polyethylene glycols, polymethylpentene, polyhydroxy alkanoates, for example such as poly(hydroxyvalerate), poly(hydroxybutyrate), poly(hydroxybutyrate-co-valerate), poly(lactic acids), poly(glycolic acids), poly(glycolide), poly(L-lactide), poly(lactide-co-glycolide), poly(glycolic acid-co-trimethylene carbonate), polyanhydrides, polyorthoesters, polyethers, polyether blocks, for example, poly(ethylene oxide), poly(trimethylene oxide), poly(propylene oxide) or poly(tetramethylene oxide) blocks, one specific example of which is a poly(tetramethylene oxide)- -polyamide-12 block copolymer, polyoctenamers, a mixture of cyclic and linear polyoctenamers, poly(caprolactone), poly(trimethylene carbonate), polyester amide, co-poly(ether-esters) (e.g. PEO/PLA), polyphosphazenes, ethylene-vinylalcohol copolymer, biomolecules (such as fibrin, fibrinogen, cellulose, starch and collagen), hydrophilic polymers such as the hydrophilic hydrogels, cross-linked polyvinyl alcohol, natural rubber, neoprene rubber, butyl rubber, hydroxyl-terminated organopolysiloxanes of the room temperature vulcanizing type which harden to elastomers at room temperature following the addition of cross-linking agents in the presence of curing catalysts, one- or two-component dimethylpolysiloxane compositions cured by hydrosilylation at room temperature or under elevated temperatures, as well as any mixtures thereof.

Polysiloxanes, in particular poly(dimethyl siloxane) (PDMS), are highly suitable for use as a membrane regulating the permeation rate of bioactive agents. Polysiloxanes are physiologically inert, and a wide group of drugs are capable of penetrating polysiloxane membranes, which also have the required strength properties.

The structural integrity of the material may be enhanced by the addition of a particulate material such as silica or diatomaceous earth. The elastomers can also be mixed with other additives, for example to adjust elastomer's hydrophilic or hydrophobic properties, while taking into account that all additives need to be biocompatible and harmless to the patient. The core or membrane may also comprise additional material to further adjust the release rate of one or several of the therapeutic substances, for example complex forming agents such as cyclodextrin derivatives to adjust the initial burst of the substance to the accepted or desired level. Auxiliary substances, for example such as tensides, antifoaming agents, solubilisers or absorption retarders, or a mixture of any two or more of such substances, can also be added in order to impart the desired physical properties to the body of the delivery system. Further, additives such as pigments, glossing agents, matting agents, colorants, mica or equal can be added to the body of the delivery system or the membrane or to both in order to provide the delivery system with a desired visual appearance.

The incorporation of the matrix comprising NFC and at least one bioactive agent into a final formulation or reservoir, in combination with suitable support materials, such as polymers, and additives and the like may be carried out by following (not limiting) methods to a desired form: coating extrusion (single or multiple coating), compression molding, over molding, lamination, injection molding, spray coating, dipping, plasma coating, blending, loading etc. The final formulation may be additionally coated with a polymer, such as a biodegradable polymer, for example polylactide or the like. The reservoir may also be a tube or container of any desired size and form, encasing the matrix forming the core of the system.

The intrauterine delivery system (IUD) according to the invention can be manufactured in any size as required, the exact size being dependent on the mammal and particular application. In practice, the dimensions of the delivery system should be close to the size of the uterine cavity. For human female an outer diameter of the frame is typically from 18 to 42 mm, preferably from 20 to 38 mm or from 22 to 36 mm. The cross sectional diameter is typically from 0.5 to 10 mm, preferably from 1 to 6 mm and more preferably from about 1.5 to 4 mm.

Typically the outer diameter of the reservoir may vary from 0.5 to 5 mm, preferably from 1 to 3.5 mm. If the reservoir is manufactured by coating methods, the wall thickness can be from 0.01 to about 5 mm, preferably from 0.2 to 3.5 mm. The length of the conventional reservoir may vary from 5 mm to 50 mm, preferably from 15 to 38 mm. If the reservoir comprises more than one core, the length of the cores is chosen to give the required performance and is for example from 5 to 35 mm.

The thickness of the polymer layer, the membrane or the film, encasing the core is such that it can be manufactured within acceptable tolerances by methods known in the art and conveniently lies within the range of from 0.01 to 1.0 mm, preferably from 0.1 to 0.6 mm. The thickness of a polymer layer separating the cores can be about from 0.01 to 5 mm, preferably from 1 to 5 mm and depends on the nature of the material and its capacity to prevent permeation of the active materials from one core to the other.

The vaginal delivery system (IVR) according to the invention can be manufactured in any size as required, the exact size is being dependent on the mammal and particular application. In practice, for a human female an outer ring diameter is typically from 35 to 70 mm, preferably from 35 to 58 mm or from 45 to 65 mm and more preferably from 50 to 58 mm. The cross sectional diameter is typically from 1 to 10 mm. In a particular embodiment the cross sectional diameter is between 2 and 6 mm, in a specific embodiment between about 3.0 and 5.5 mm and in another embodiment between about 3.5 and 4.5 mm and in yet another embodiment is between 4.0 and 5.0 mm.

The diameter of a cavity or an inert supporting member inside the delivery system, if any, varies in the range of from 0.5 mm to 3 mm, and the layer containing the active substance has a thickness of 0.1 to 5.0 mm, preferably 0.2 to 3.5 mm.

The amount of the therapeutically active substance incorporated in the core varies depending on the particular therapeutically active substance, the desired therapeutic effect and the time for which the system is expected to provide therapy. Reservoirs with varying sizes and shapes can be formulated for administering dosages for different therapeutical areas. The upper limit on the amount of therapeutically active substance depends on the size of the reservoir. The lower limit depends on the activity of the therapeutically active substance and on the expected release time. A person skilled in the art is readily able to determine the amount of the therapeutically active substance needed for each specific application of the delivery system. Preferably, the amount of therapeutically active substance particularly in intrauterine and vaginal delivery systems varies between 0.01 to 60 wt-%, when it is mixed into the polymer composition, the preferred amount being between 5-50 wt-%. Other possible ranges of the amount of the therapeutically active substance are 0.5-60 wt-%, 5-55 wt-%, 10-50 wt-%, 25-60 wt-%, 40-50 wt-% and 15-35 wt-%.

Preferably the poly(alkylene oxide) groups mentioned above are poly(ethylene oxide) (PEO) groups. In the polymer composition of the core or the membrane the proportion of the polysiloxane comprising poly (alkylene oxide) groups, for example polydimethylsiloxane comprising poly (ethylene oxide) groups as alkoxy-terminated grafts or as blocks that are linked to the polysiloxane units by silicon-carbon bonds (PEO-b-PDMS copolymer), vary from zero to 80% of the total amount of polymers, but can naturally be higher.

Other possible ranges for the proportion of the polysiloxane comprising poly (alkylene oxide) groups are from 5 to 60% or from 10 to 50%, preferably from 10 to 45% and more preferably from 20 to 40% of the amount of polymer composition.

Because of the many unique properties of NFC, it is particularly suitable as a matrix material for sustained delivery of bioactive agents. It is non-toxic and bio-stabile, i.e. it forms a uniform matrix which does not fragment, and it does not swell as other hydrogels usually do. The matrix structure is simple, is applicable even without any supporting membrane, and can be formulated in different shapes, for example as a sandwich type matrix. NFC matrices are compatible and suitable for a large range of bioactive agents and materials including hydrophobic molecules, hydrophilic molecules, peptides and proteins.

Biocompatibility and durability are of outmost importance, together with intended release profiles and/or geometrical dimensions of the obtained device. According to the present invention adjustable and predetermined release profiles of bioactive agents may be achieved, while simultaneously extensive bioadhesion can be avoided with biocompatible delivery systems.

The following examples are illustrative of embodiments of the present invention, as described above, and they are not meant to limit the invention in any way.

EXAMPLES

Example 1

Manufacture of NFC Materials

The following NFC materials were used in the Examples: Native NFC (Sample 1) and anionic NFC (Sample 2).

Sample 1: The native NFC was made from bleached cellulose pulp by high pressure homogenization using industrial fluidizer for fibrillation. The raw material was aseptically collected from a pulp mill and thoroughly purified prior to the homogenization with sterilized machinery. Thus, the microbial purity was maintained through the whole production process. The purified pulp fibers were diluted with sterilized, ultra high quality water before the fibrillation. The nanofiber concentration of the resulting hydrogel is typically 1.7 wt %. The nanofiber hydrogel was autoclaved (121° C./20 min) directly after fibrillation.

Sample 2: The anionic NFC was prepared from the same cellulose pulp material, using similar fibrillation technique as described above, but the cellulose pulp was anionically modified prior to the fibrillation. The anionic modification is based on oxidation of cellulose pulp. Due to the modification, the cellulose pulp is easy to disintegrate to cellulose nanofibers. Also, the labilization reaction brings aldehyde and carboxylic acid functionalities on the surface anionic cellulose nanofibers, which increases the hydrophilicity of the material. WO 09/084566 and JP 20070340371 disclose such modifications. The oxidized cellulose pulp was thoroughly purified after the chemical modification. The purified fibers were diluted with sterilized, ultra high quality water before the fibrillation. The NFC concentration of the resulting hydrogel is typically 0.7 wt %. The NFC hydrogel was autoclaved (121° C./20 min) directly after fibrillation.

Figure 2:
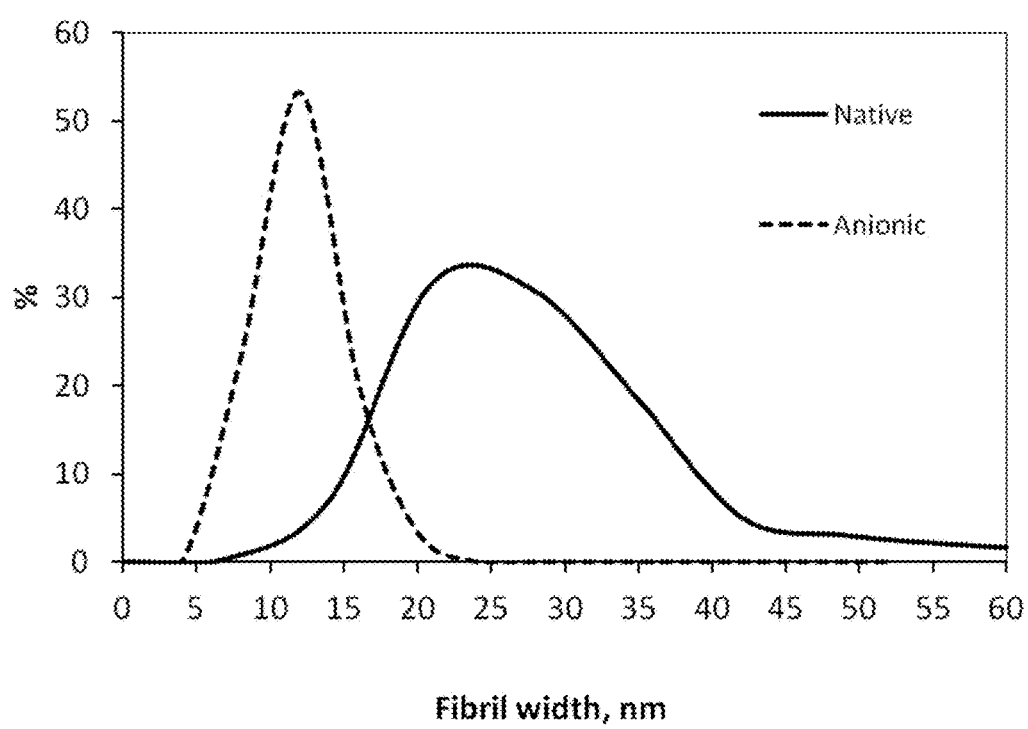
FIG. 2 illustrates typical nanofiber width distribution of samples 1 and 2. Distributions are measured from SEM images.

Cryo-TEM images of native NFC and anionic NFC are presented in FIG. 1. Native NFC hydrogel is composed of a mixture of individual cellulose nanofibrils and fiber bundles (1A). The diameter of smallest fibers is approximately 7 nm, majority of the cellulose material forms 50-100 nm in bundled structures, however. The exact length scale cannot be estimated from the images due to entangled and bundled nature of the material, but it seems clear that individual nanofibers are several micrometers long. The cryo-TEM image of the anionic NFC hydrogel (1B) shows homogeneously distributed individual cellulose nanofiber network. The diameter of these nanofibers is approximately 7 nm and the length exceeds a micrometer. The nanofibers have 100-200 nm long straight segments followed by sharp kinks along the fiber axel. These straight segments are composed of highly crystalline cellulose domains—the bending sites are formed by the amorphous parts. Typical nanofiber width distribution of samples 1 and 2 are presented in FIG. 2. The distribution is calculated from SEM images and thus the actual sizes may differ from these values due to aggregation during SEM imaging.

Example 2

Manufacture of NFC Matrices for Controlled Drug Delivery Containing Indomethacin or Itraconazole or Beclomethasone Dipropionate 1.66 wt % aqueous NFC suspension (UPM-Kymmene Corporation, Finland), indomethacin (Hawkins, Inc. USA), itraconazole (Apotecnia SA, Murcia, Spain) and beclomethasone dipropionate (Sigma-Aldrich, Germany) were used in the example.

All three compounds are practically insoluble in water (solubility <1 μg/ml). This property often presents an obstacle in formulation design. However this characteristic was used as an advantage since the matrix production involved filtration step in which drug was supposed to remain in filtration mass but not go through the filter. The same production method was applied for preparation of matrix systems containing all three drugs. Highly viscous aqueous suspension of NFC was mixed with the drug in ratios given in Table 1, where the content of NFC/Indomethacin, NFC/Itraconazole and NFC/beclomethasone suspensions used for matrix production are shown. The numbers are mass fractions of drug and fibers used in the initial suspensions. Labels for the different formulations are also given in the table. The numbers are mass fractions used in the initial suspensions. Labels for the different formulations are also given in the table. The mixture was sonicated for 2 min using high intensity ultrasound processor equipped with 2 mm stepped microprobe. Following settings were used: power 750 W, frequency 20 kHz and amplitude 20%. Prepared mixture was diluted with water in ratio (1:1). Suspension was then filtered through a PVDF membrane filter with diameter of 47 mm and 0.2 µm pore size. During the filtration process water insoluble drug particles remained on the filter and were entrapped within network of fine cellulose fibres. After the filtration, the wet matrices were dried in the oven for 4 h at temperature of 65° C. Filtrate was collected and the amount of drug that had passed through the filter was determined by a suitable HPLC method.

Drug loadings were calculated as the difference in the amount of drug used for the preparation of the suspensions and the amount of drug that was lost during the filtration and in the surface fractions of the drugs that were dissolved during the first 24 h of the dissolution test. Table 2 shows production loss, surface fraction of the drug and final loading degrees of NFC/Indomethacin, NFC/Itraconazole, modified NFC/Itraconazole and NFC/Beclomethasone matrices. All values are in mass percentages. Indomethacin has a higher solubility in water than itraconazole and beclomethasone, which caused a slightly higher portion of indomethacin to be lost during the filtration. Further, in the case of beclomethasone matrices, a higher amount of the drug was located on the matrix surface. Therefore, beclomethasone matrices have slightly lower loading degrees compared to itraconazole matrices (Table 2) showing production loss, surface fraction of the drug and final loading degrees of NFC/Indomethacin, NFC/Itraconazole, NFC/Beclomethasone matrices. All values are in mass percentages.

TABLE 1

| API/NFC (%/%) | Indomethacin | Itraconazole | Beclomethasone dipropionate |
|---|---|---|---|
| 20/80 | INDO20 | ITRA20 | BECLO20 |
| 30/70 | INDO30 | ITRA30 | BECLO30 |
| 40/60 | INDO40 | ITRA40 | BECLO40 |
| 50/50 | INDO50 | ITRA50 | BECLO50 |
| 60/40 | INDO60 | ITRA60 | BECLO60 |

TABLE 2

| Batch | *Production loss (%) | *Drug surface fraction (%) | **Final loading (%) |
|---|---|---|---|
| ITRA20 | <0.1 | 1.5 | 19.8 |
| ITRA30 | <0.1 | 1.2 | 29.8 |
| ITRA40 | <0.1 | 2.0 | 39.5 |
| INDO20 | 1.1 | 14.0 | 17.7 |
| INDO30 | 0.9 | 10.7 | 27.7 |
| INDO40 | 0.8 | 11.7 | 37.0 |
| BECLO20 | <0.1 | 16.6 | 17.3 |
| BECLO30 | <0.1 | 14.8 | 26.8 |
| BECLO40 | <0.1 | 28.2 | 32.4 |

*Values calculated as a percentage of drug mass compared to the total mass of drug used (100% represents the total amount of drug used in the production)
**Values calculated as a percentage of drug mass compared to the total mass of the matrix system (100% represents the total mass of matrix system)

Figure 3:
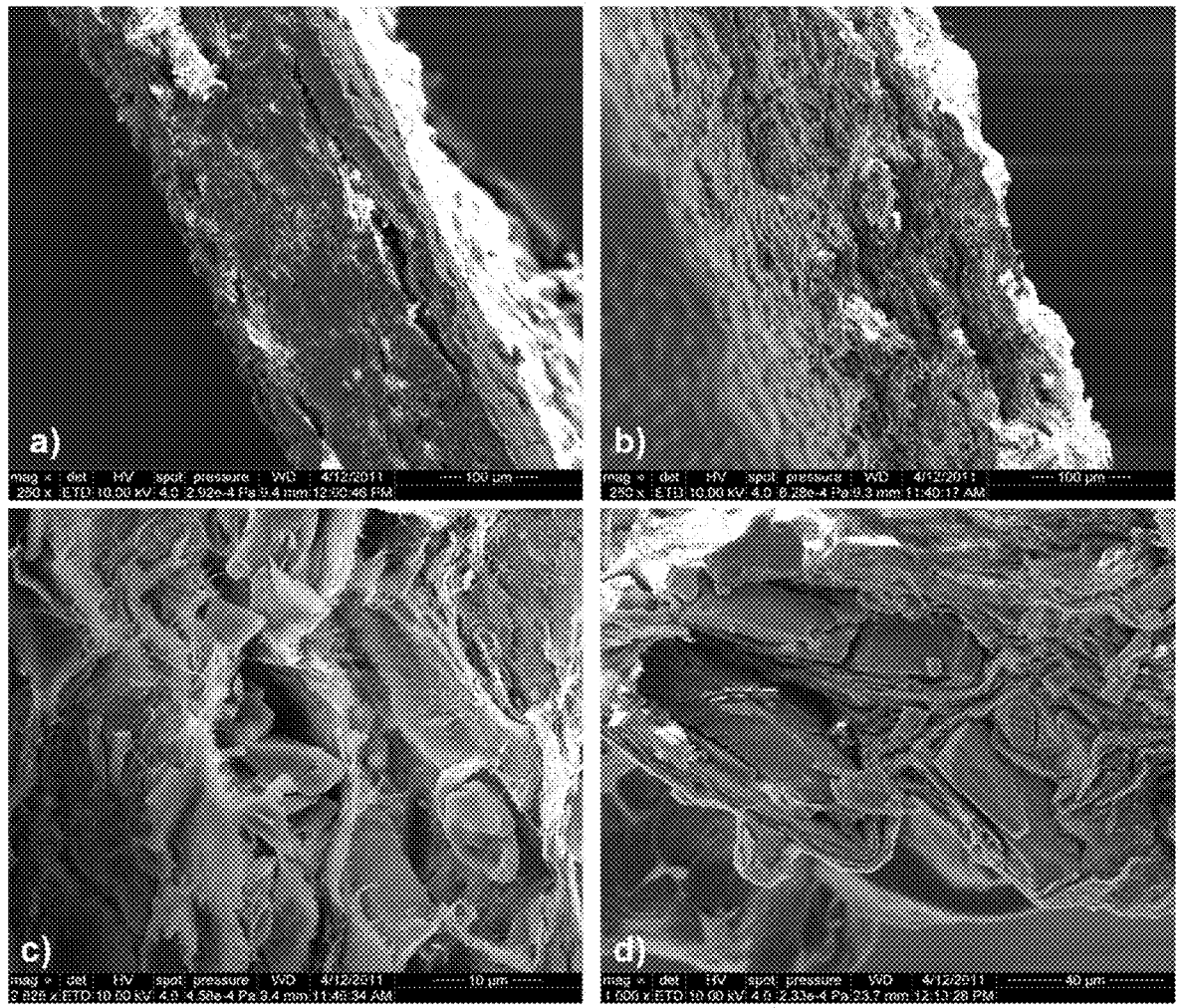
FIG. 3 presents SEM images of matrix cross sections: a) a matrix containing 40% of indomethacin cut by a scalpel (magnification 200×), b) a matrix containing 40% of itraconazole cut by a scalpel (magnification 250×), c) a matrix containing 40% of indomethacin broken manually (magnification 1500×), d) a matrix containing 40% of itraconazole broken manually (magnification 3000×).

Matrix structure (morphology) was studies using SEM. Micrographs of cross sections of indomethacin and itraconazole loaded matrices were obtained using FEI Quanta™ FEG scanning electron microscope. The samples were prepared in two different ways. For analysis of inner matrix structure, the matrices were broken manually. For thickness determination, the matrices were cut with a scalpel to obtain a flat and smooth cross section surface. In both cases, the samples were fixed onto two-sided carbon tape with silicone adhesive and sputtered with platinum for 25 seconds with an Agar sputter device. FIGS. 3(a) and (b) show the SEM images of cross section of the itraconazole and indomethacin loaded matrices that contained 40% of drug. 3(a)-(d) were made of unmodified NFC. The samples shown in the FIGS. 3(a) and (b) were prepared by cutting matrices with a scalpel. This produced a smooth surface and prevented capping and lamination that occur when matrices are broken manually. Thus the matrix thickness could be easily determined. As was mentioned above, the matrix thickness is dependent on the concentration of the suspension used in the production. Higher concentrations of NFC and/or drug lead to an increase in the matrix thickness. In this way, the thickness can be tailored by choosing different concentrations. The concentration chosen for the production of itraconazole and indomethacin loaded matrices resulted in thicknesses in the range of 150-200 µm. The thickness affects the mechanical properties of the matrices. Films made of pure NFC with a thickness of 60 µm are very soft and can be folded as conventional paper, but possess excellent mechanical properties. The elasticity provides easy handling and shape tailoring if needed (e.g. slices, squares), since the matrices could be easily cut by scissors. FIGS. 3(c) and (d) present cross sections of matrices that were broken manually in order to provide imaging of cross section morphology and FIGS. 3(e) and (f) cross section of itraconazole loaded matrices made of modified NFC. NFC fibers orientate and organize in lamellar phases during the filtration process forming multiple thin layers around the entrapped drug particles. Size of the drug particles within the matrix is different for indomethacin and itraconazole and corresponds to the particle size of the starting materials since production process did not include reduction of the particle size.

Thermal properties of the matrix systems were measured by DSC. Differential scanning calorimetry (DSC) of drug loaded matrices was carried out using differential scanning calorimeter Mettler Toledo DSC 823e. The samples were placed in aluminum pans and heated at a scanning rate of 10° C./min between 25-200° C. The matrix samples were compared to pure drug samples that were analyzed using same settings. DSC thermogram of pure indomethacin (FIG. 4) shows sharp endothermic peak at 160° C., which corresponds to the melting temperature of crystalline γ-indomethacin. A broadened peak of the crystalline drug can be detected in DSC profiles of matrix systems as well indicating the presence of γ form of crystalline indomethacin. Similar behaviour is observed in the case of itraconazole and beclomethasone samples where the pure drugs give sharp peaks representing crystalline form of drug. The endothermic peaks are observed for the itraconazole and beclomethasone loaded matrices at the same temperature as pure drugs. The results show that the matrix production process does not affect the physical state of the drug in high extent and crystalline lattice remains intact.

In order to confirm the physical state of the drug in the matrices, X-ray diffraction studies of the drug alone, blank matrices and drug-loaded matrices were carried out. The XRPD was performed using the theta-theta diffractometer. The angular range was from 5° to 40° and the measuring time was 15 min/sample. Crystallinity of the samples was estimated by fitting the intensity of the matrix samples and the intensity of the membranes made of pure NFC to the experimental intensity curve. X-ray diffractograms of the samples described above showed that the drug is still present in its crystalline form (FIG. 5). Intensity of the peaks is decreasing with decreased loading degree. Decreasing intensity of the peaks is a consequence of the experimental method used, since the mass of the analyzed samples was constant in all cases but the samples had different loading degrees and thus contained lower amounts of drug.

Figure 6:
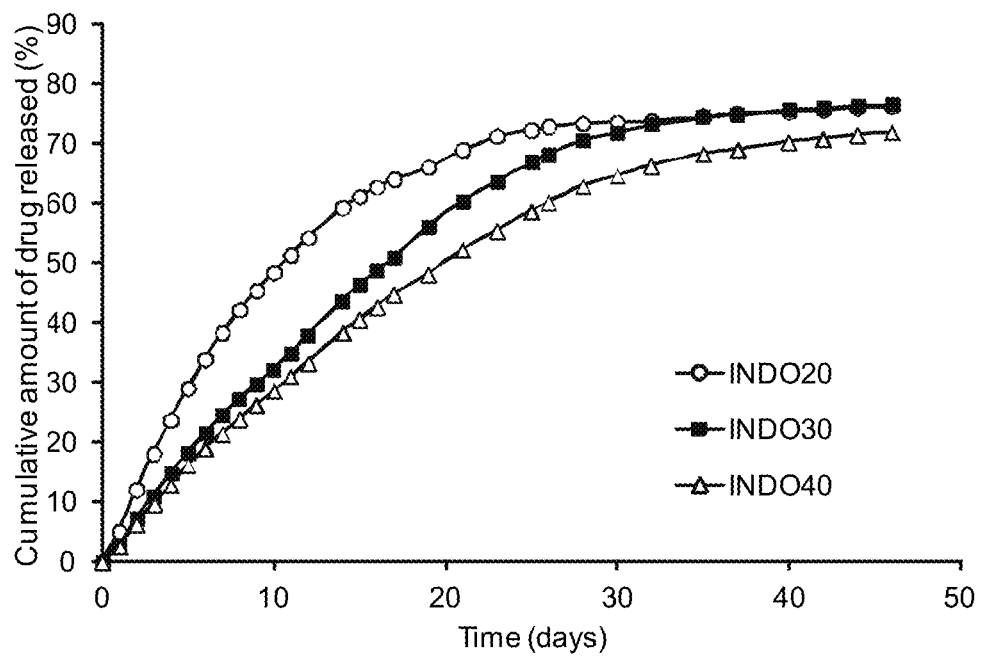
FIG. 6 shows the release profiles of indomethacin containing matrices.
Figure 7:
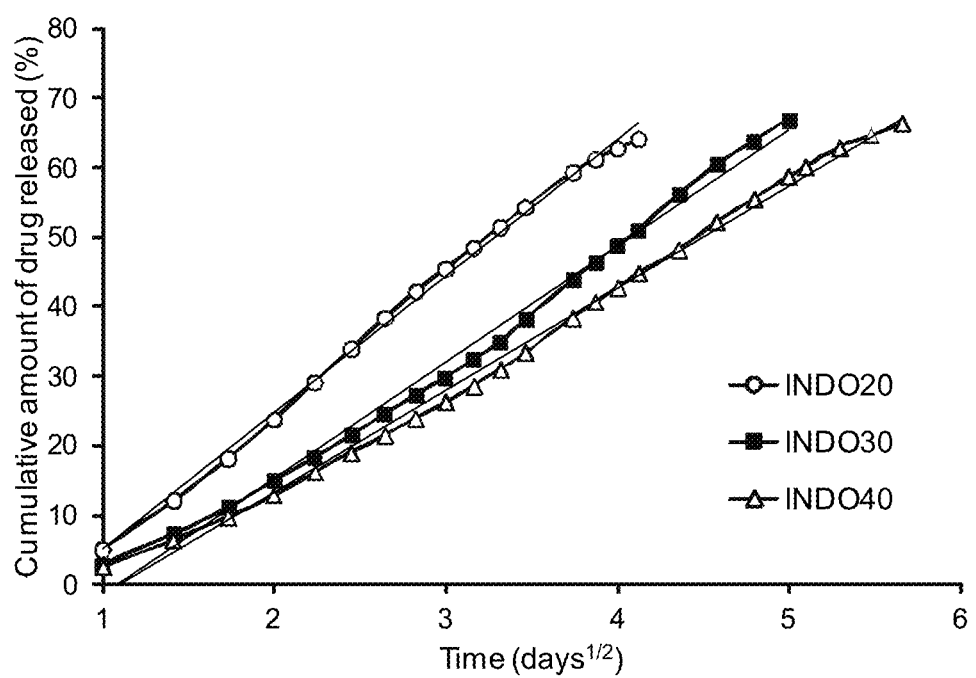
FIG. 7 fits equation (3b) to the data in FIG. 6. Only the time points corresponding to releases of less than 65% are used, since the dissolution curves level off after that. Lines represent the theoretical release curves.

Drug release studies were carried out to determine diffusion limited release from matrices. In dissolution rate determination, pieces of the matrix systems (4.5 mg) were cut and placed into vessels of standard dissolution equipment (paddle method, Ph. Eur. 7$^{th}$) that contained 400 ml of a medium. Medium was chosen based on the solubility of the drug. In the case of indomethacin phosphate buffer pH 5.0 was used as the medium and for itraconazole loaded matrices 2 g/l aqueous solution of NaCl, pH 1.2 while for beclomethsone matrices dissolution medium was 1% (w/w) hydroxypropyl beta cyclodextrin. The matrices were left in the medium overnight with paddle rotation speed of 60 rpm to remove the fraction of the drug located on the surface. Matrices were then transferred to 50 ml glass bottles with 25 ml of medium and placed into a shaking water bath equipped with a tray for Erlenmeyer flasks. Shaking frequency was set to 100 min$^{-1}$. Samples of the medium were taken at various time points and analyzed by suitable HPLC method to determine the released amount of drug. Three parallel measurements were performed. FIG. 6 shows the release profiles of indomethacin containing matrices. Since the matrices are flat and have a large aspect ratio of length to thickness, their release can be modeled with a simple Higuchi equation $$Q = A\sqrt{\frac{D\varepsilon}{\tau}(2\rho - \varepsilon C_s)C_s t} \quad (1)$$

where Q is the amount of drug released, A is the surface area of the matrix, D is the diffusion coefficient of the drug inside the matrix, E is the porosity of the matrix, T is tortuosity of the matrix, p is the density of the drug material in the matrix, $C_s$ is the saturated solubility of the drug inside the matrix and t is time. The density of the drug in the above equation can be assumed to be $$\rho = f \rho_{IND} \quad (2)$$

where f is the volume fraction of the drug in the matrix and $\rho_{IND}$ is the density of indomethacin. Assuming that the drug has low solubility in water, i.e. $\mu \gg C_s$, the equation (1) reduces to $$Q = A\sqrt{2\frac{D\varepsilon}{\tau}\rho C_s t} \quad (3a)$$

$$\frac{Q}{Q_\infty} = \frac{A\sqrt{2\frac{D\varepsilon}{\tau}\rho C_s t}}{V_\rho} = \frac{1}{h}\sqrt{2\frac{D\varepsilon}{\tau}\frac{1}{f\rho_{IND}}C_s t} \quad (3b)$$

where V is the volume and h is the thickness of the matrix. The equation (3b) was used to fit the data in FIG. 6. The results are shown in FIG. 7 and the fitting parameters for the theoretical release curves used in FIG. 7 are shown in Table 3.

TABLE 3

| Loading (%) | Slope | R$^2$ | ε/T:(ε/T)$_{IND20}$ |
|---|---|---|---|
| 17.7 | 19.688 | 0.997 | 1 |
| 27.7 | 17.46 | 0.996 | 1.230812 |
| 37 | 14.698 | 0, .995 | 1.165042 |

The data fits very well the Higuchi equation, indicating diffusion limited release, although the diffusion in this case is very slow (with 1 mm$^2$ surface area, this would be in the region of 10$^{-12}$ m$^2$/s, but it is difficult to give exact values).

Slopes of the fits can be used to estimate the difference in the porosity/tortuosity factor in eq. (3b) as per eq (4).

$$\frac{\text{slope}_1}{\text{slope}_2} = \frac{h_2}{h_1}\sqrt{\frac{\varepsilon_1/\tau_1}{\varepsilon_2/\tau_2}\frac{f_2}{f_1}} \quad (4)$$

Here the thickness is assumed to be the same in all cases and the volume fraction f is assumed to be linearly dependent on the mass fraction of the drug inside the matrix (φ), although this is completely valid only when the density of the drug and the matrix are similar. The result indicates that the apparent diffusion in the INDO30 and INDO40 samples is faster than in the INDO20 sample due to larger porosity or lower tortuosity, i.e. the matrix is more "open". The difference in the release rates of INDO30 and INDO40 seems to be mostly due to the different drug volume fractions. This is also apparent when plotting Q/Q∞*φ$^{1/2}$ vs t$^{1/2}$. Curiously, the release seems to be a bit slow in the beginning for all samples. This seems to be the clearest in the case of INDO40 sample and least apparent in the INDO20 sample. This could be an indication that it takes some time for water to diffuse into the matrix and start dissolving the drug.

Figure 8:
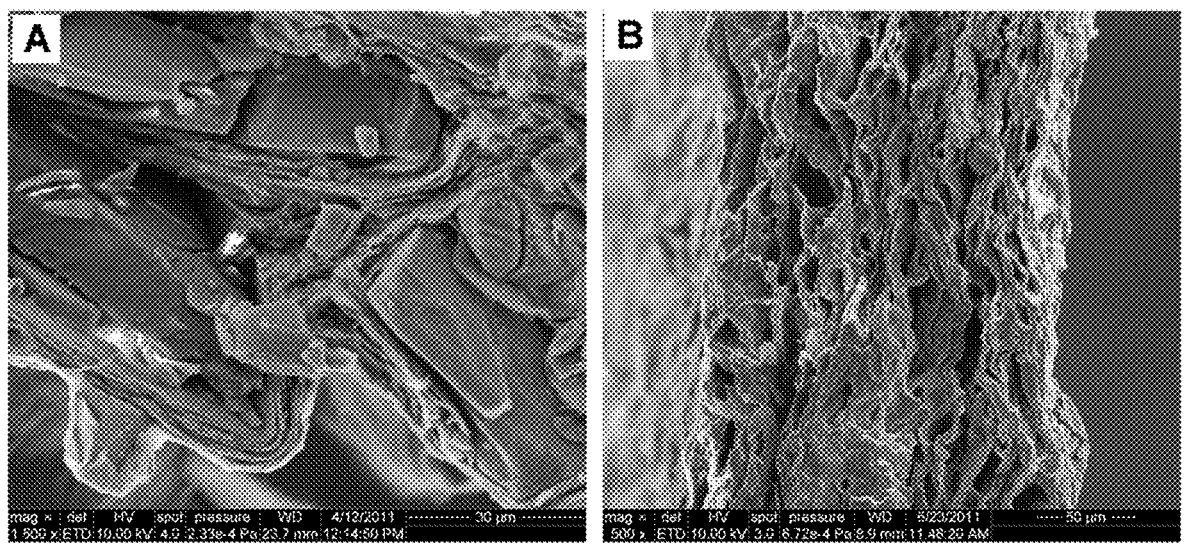
FIG. 8 shows SEM images of cross section of matrix containing 40% of indomethacin before (A) and after (B) the drug release.

FIG. 8 shows cross-section of indomethacin loaded matrices before and after drug release. The matrix shape and thickness remain unchanged after drug is released leaving the highly porous structure.

Figure 9:
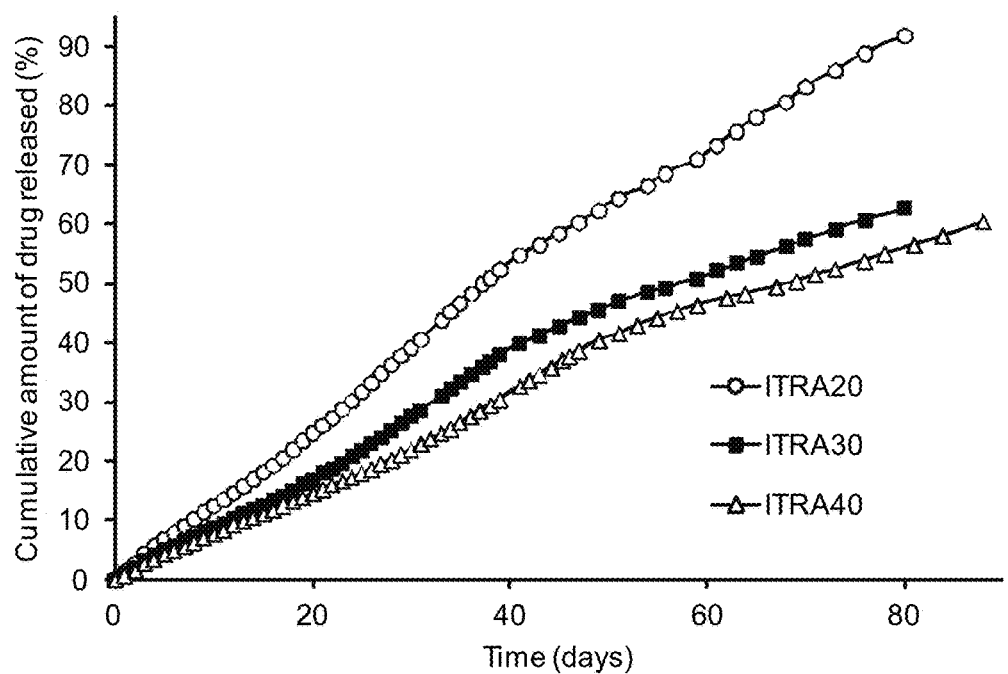
FIG. 9 shows drug release profiles from of NFC/Itraconazole matrices.
Figure 10:
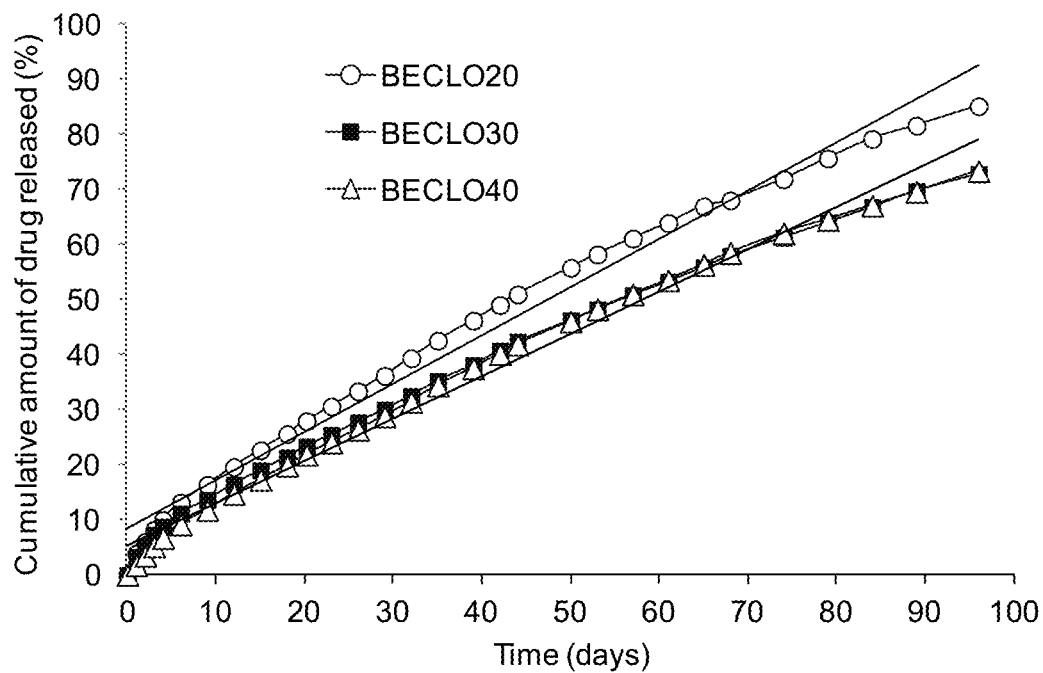
FIG. 10 shows drug release profiles of NFC/Beclomethasone dipropionate matrices

FIG. 9 shows release profiles of itraconazole matrices and FIG. 10 release profiles of beclomethasone matrices. The shape of the dissolution curves differs from the indomethacin matrices and thus releasing kinetics are most likely different. The itraconazole and beclomethasone matrices release drug slower giving constant controlled release over period of three months. Higuchi model applied in the case of indomethacin matrices will not apply here and obviously the release is not controlled by simple drug diffusion from the matrix system. The release from itraconazole matrices is closest described by zero order kinetics (R$^2$>0.9863) as well as in case of beclomethasone matrices (R$^2$>0.9822). It can be assumed that all matrices have the same thickness and thus this parameter cannot be considered to be the reason for the difference in the release profiles. As mentioned above, the particle size of the incorporated drug is different. Itraconazole particles are smaller and the dissolution of small evenly distributed particles causes an increased tortuosity of itraconazole matrices compared to indomethacin ones. Further, larger indomethacin particles could cause more disruption in the lamellar structure of the NFC matrices, making them looser.

Besides the particle size, wetting properties of two systems seem to be different. This is confirmed by contact angle measurements where contact angle between matrix surface and water drop is measured (Table 4). Surface of indomethacin matrices is more hydrophilic leading to faster wetting and water diffusion into the matrix. Furthermore, pH value of medium used for dissolution test has an influence on behavior of NFC. NFC is slightly negatively charged in neutral surrounding. The charge originates from carboxylic groups of hemicellulose residues that are present in the material. pKa value of these carboxylic groups is 3.7. Therefore pH value 5 of dissolution medium used for indomethacin matrices will lead to a higher portion of these carboxylic groups to be in ionized form. This causes the repulsion between neighbouring NFC fibres or matrix layers leading to easier water permeation and matrix swelling and consequently to faster drug release compared to dissolution medium used for itraconazole matrices which pH value was 1.2. This effect is even more pronounced in case of modified NFC/Itraconazole matrices since modified NFC fibres have high content of carboxylic residues on the surface. This leads to an extensive matrix swelling when placed in pure water. However at pH of dissolution medium (1.2) swelling process is limited. All previously mentioned factors lead to slower release from itraconazole and beclomethasone matrices compared to the indomethacin matrices. However the influence of these factors is not completely clear and is a subject of ongoing research.

TABLE 4

| Sample | Contact angle |
| --- | --- |
| INDO20 | 42.4 |
| INDO30 | 35.6 |
| INDO40 | 10.5 |
| ITRA20 | 50.7 |
| ITRA30 | 51.2 |
| ITRA40 | 52.7 |
| BECLO20 | 46.2 |
| BECLO30 | 31.3 |
| BECLO40 | 13.2 |
| Indomethacin | 76.7 |
| Itraconazole | 107 |
| Beclomethasone | 78.7 |

Example 3

NFC Matrices Incorporated in PDMS/PEO Tubes for Controlled Drug Delivery Containing Indomethacin Matrices were produced by using indomethacin as model compound. The matrices were produced using the method of filtration and drying described in EXAMPLE 2.

Slices of matrix were cut and placed into the 3 cm long tubes made of polydimethylsiloxane/polyethylene oxide (PDMS/PEO) and tubes sealed from both ends using silicone adhesive.

PDMS-b-PEO tubes 50:50
outer diameter: 2.453 mm
inner diameter: 1.98 mm
wall thickness: 0.2365 mm
PEO-b-PDMS/PDMS 5510
outer diameter: 2.96 mm
inner diameter: 2.38 mm
wall thickness: 0.29 mm The dissolution test was performed after matrix systems were packed into the elastomer tubes made of polydimethylsiloxane-b-polyethylene oxide copolymer (PDMS-b-PEO) and PDMS. PDMS-b-PEO is copolymer of different ratios of PDMS and PEO. Two different types of tubes were used which differed in PDMS/PDMS-b-PEO ratio. Slices of INDO40 matrix were cut and placed into the selected tubes. Tubes were sealed with a silicone adhesive and placed into the 100 ml glass bottles with 50 ml of medium and placed into a shaking water bath.

The release studies from prepared systems were conducted. The tubes with matrices were placed into 100 ml bottles with 50 ml of dissolution medium (phosphate buffer pH 5.0) and placed into a shaking water bath. Samples of the medium were taken at various time points and analyzed by suitable HPLC method to determine the released amount of drug. Three parallel measurements were performed. After each sampling the total amount of dissolution medium was replaced with the fresh medium.

Figure 11:
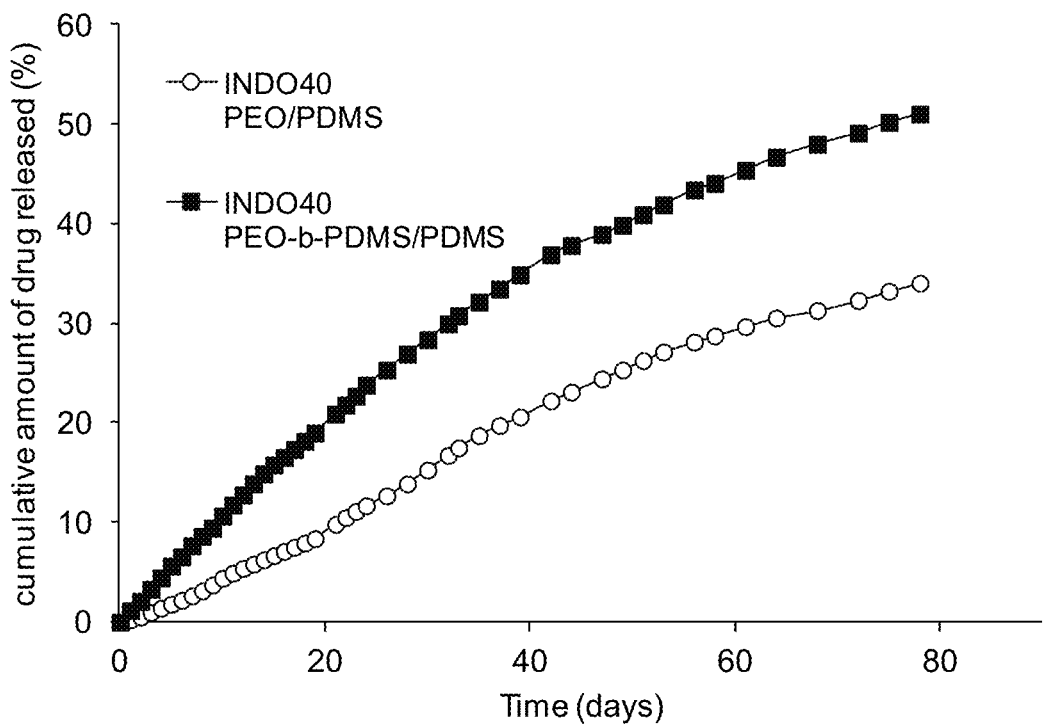
FIG. 11 presents drug release profiles of the INDO40/PDMS/PEO tubes systems.

Dissolution curves showing the release from the INDO40/PDMS/PEO tubes systems are shown in FIG. 11. Both systems give slower release than the matrix systems alone. Furthermore, even though the drug surface fraction was not washed in this case no burst effect could be seen and the drug release starts immediately with no lag time. This is due to the fact that tubes also have contribution in controlling drug release. These results prove that prepared matrices could be used in combination with currently used materials to further tailor drug releasing profiles.

Example 4

Manufacture of Anionic NFC Matrices for Controlled Drug Delivery Containing Itraconazole Matrices were produced using 0.5% anionic NFC suspension and itraconazole as model drug. The anionic NFC fibres and drug were mixed in ratio 20%/80% (m/m). The mixture was sonicated for 2 min using high intensity ultrasound processor equipped with 2 mm stepped microprobe. Following settings were used: power 750 W, frequency 20 kHz and amplitude 20%. Prepared mixture was degassed in vacuum oven for 30 min and then casted in the molds and left to dry on the room temperature for 5 days.

Figure 12:
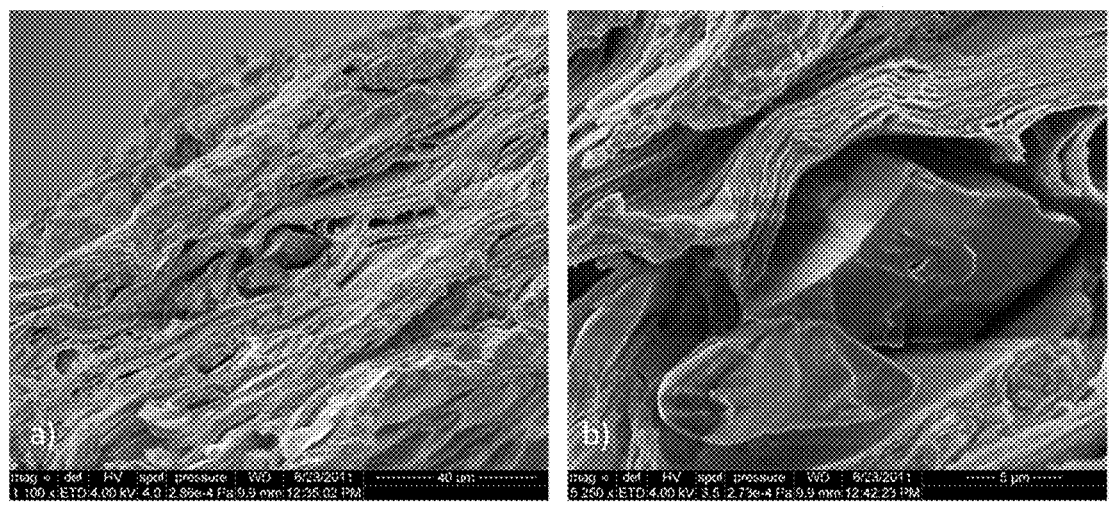
FIG. 12 presents SEM images of cross section of anionic NFC matrices containing 20% of itraconazole: a) lower magnification b) higher magnification.

Matrix structure (morphology) was studies using SEM. Micrographs of cross sections of anionic NFC/Itraconazole matrices were obtained using FEI Quanta™ FEG scanning electron microscope. The samples were fixed onto two-sided carbon tape with silicone adhesive and sputtered with platinum for 25 seconds with an Agar sputter device. As it was explained in the Example 2, the matrix thickness is dependent on the concentration of the suspension used in the production. The concentration chosen for the production of anionic NFC/Itraconazole matrices resulted in thicknesses of approximately 100 µm. The FIG. 12 shows SEM images of the inner structure of the matrices where the solid drug particles are covered with layers of anionic NFC.

Figure 13:
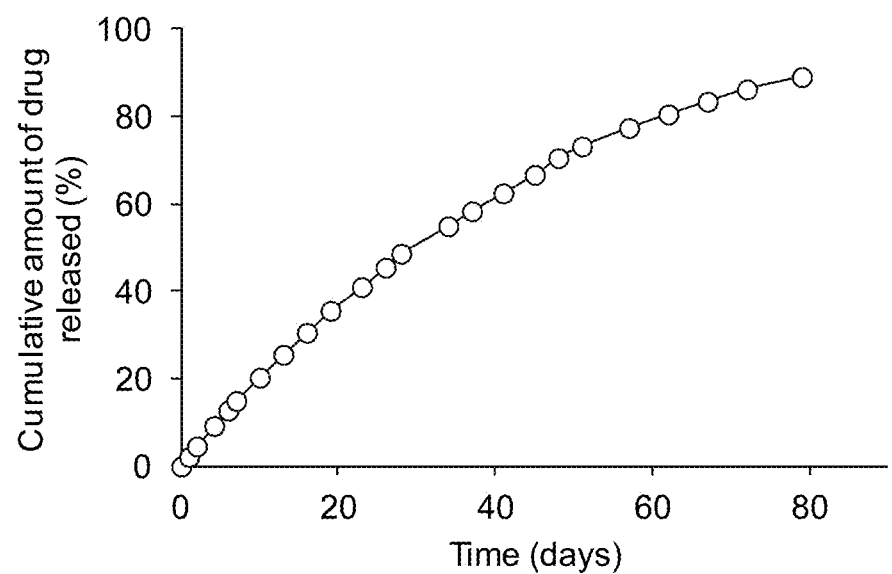
FIG. 13 shows drug release profiles of itraconazole from anionic NFC/itraconazole matrices.

For the drug release studies the pieces of matrices (3.5 mg) were cut and placed to 50 ml glass bottles with 25 ml of medium and placed into a shaking water bath equipped with a tray for Erlenmeyer flasks. Shaking frequency was set to 100 min$^{-1}$. Samples of the medium were taken at various time points and analyzed by suitable HPLC method to determine the released amount of drug. Three parallel measurements were performed. FIG. 13 shows the release profiles of itraconazole from the anionic NFC matrices.

Example 5

NFC Microparticles for Controlled Drug Delivery

Spray-dried NFC particles containing drug substances were manufactured from native NFC (UPM-Kymmene Corporation, Finland) in form of 1.66% water suspension, indomethacin, (Hawkins, Inc. USA), nadolol, atenolol, metoprolol tartrate, verapamil hydrochloride (Sigma—Aldrich, Germany) and ibuprofen (Orion Pharma, Finland).

All suspensions were prepared in same manner. First the drug was dissolved in suitable solvent. Atenolol, nadolol, metoprolol tartrate, and verapamil hydrochloride were dissolved in water and ibuprofen and indomethacin in 50 mM aqueous $NH_4OH$. Solution was then mixed with NFC suspension in way that concentration of dissolved and suspended material is 0.5%. The ratios in which NFC and drug were mixed are shown in Table 8. Since used NFC was in a form of 1.66% water dispersion, the concentration of feeding suspension and the ratios in Table 8 are calculated using content of dry fibres in NFC suspension. Prepared suspensions were sonicated for 15 min using the high intensity ultrasound processor equipped with 13 mm probe and then mixed with mechanical stirrer for 15 min at speed of 1800 rpm. Batches containing 30% and 40% of ibuprofen and atenolol were not produced since particles with aimed ratio 20/80 did not have desirable properties.

TABLE 8

| API/NFC (%/%) | Indomethacin | Metoprolol tartrate | Verapamil hydrochloride | Nadolol | Ibuprofen | Atenolol |
|---|---|---|---|---|---|---|
| 20/80 | INDO20 | METO20 | VERA20 | NADO20 | IBU20 | ATE20 |
| 30/70 | INDO30 | METO30 | VERA30 | NADO30 | */ | */ |
| 40/60 | INDO40 | METO40 | VERA40 | NADO40 | */ | */ |

*Batches containing ibuprofen and atenolol and NFC in ratio 30/70 and 40/60 were not produced Suspensions were dried using Mini spray dryer Büchi B-191. The spray dryer is equipped with two-fluid nozzle and it operates in co-current mode (the feeding suspension and the drying air flow are in the same direction). The drying was performed using following parameters: inlet temperature 220° C., outlet temperature in range from 120-127° C., spray flow 700 l/h, air pressure 7 bar, aspirator setting 95% and pump setting 18%. The feeding suspension was mixed continuously during the drying process using magnetic stirrer to prevent sedimentation of suspended cellulose nanofibres.

Micrographs of the spray dried indomethacin microparticles were obtained using Scanning electron microscope. The samples were fixed onto two-sided carbon tape and sputtered with platinum for 25 seconds with an Agar sputter device. The images of metoprolol and verapamil microparticles were obtained using FEI Quanta™ FEG scanning electron microscope. The samples were prepared in same way as indomethacin samples. The micrographs were used for morphological characterization and particle size determination.

TEM images of microparticles were obtained using FEI Tecnai F12. Microparticles dispersions were dried on Formvar film-coated copper grids with a mesh size of 300. The images were used for microparticle characterization after the dissolution test.

Figure 14:
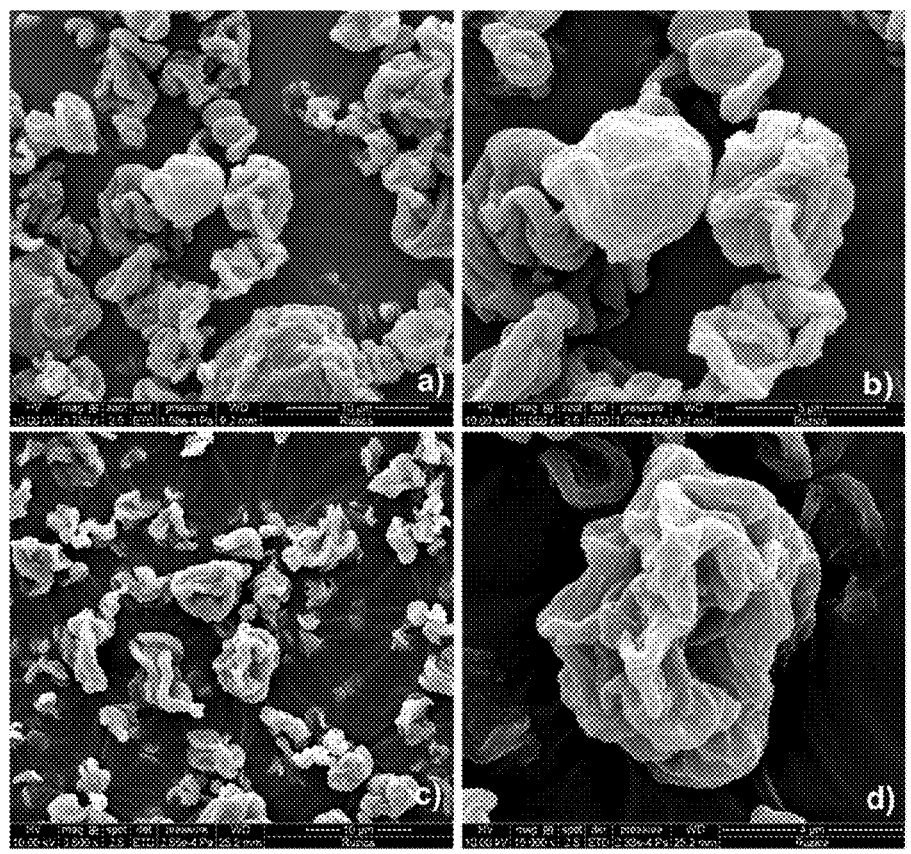
FIG. 14 shows SEM images of spray dried microparticles containing metoprolol with lower a) and higher magnification b) and verapamil with lower c) and higher magnification d).
Figure 15:
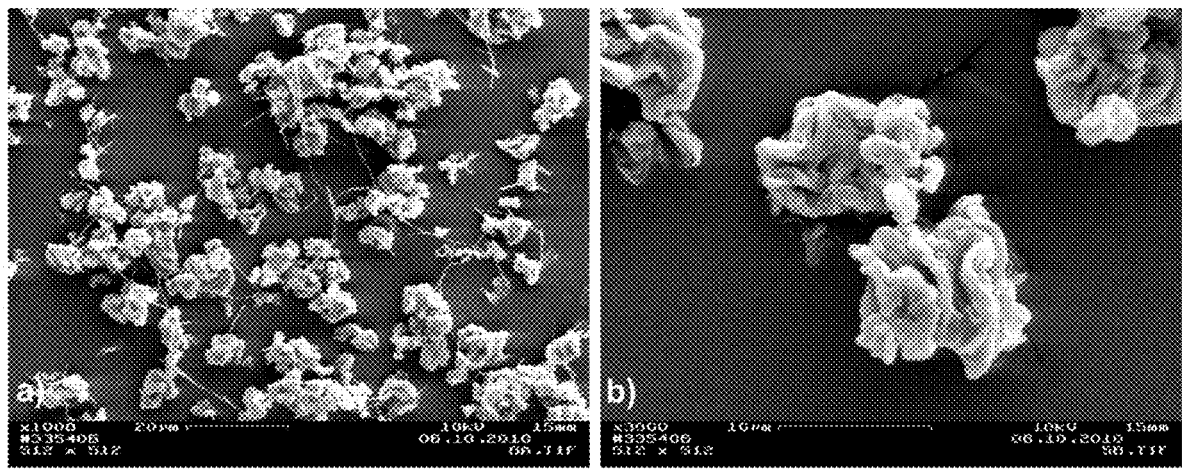
FIG. 15 presents SEM images of spray dried particles containing indomethacin with lower a) and higher magnification b).

SEM images of the produced particles (FIGS. 14 and 15) show irregular, roughly spherical, particle shape with sizes around 5 µm. Particle shape of unloaded NFC particles with the same method had similar shape and size as the drug loaded ones. However, in this case, the most interesting characteristics observed were related to the spray-dried microparticle surfaces where higher magnification reveals the fibrous structure of the particle surface. In the case of indomethacin loaded powders, certain amount of indomethacin was present as free drug that had dried separately. This can be seen in FIG. 15 as needle-like precipitates. This phenomenon was not seen when verapamil and metoprolol were used (FIG. 14). This is possibly a consequence of indomethacin precipitation that occurred before spraying process when the drug solution was added to NFC suspension.

Spray dried particles were assayed for drug content dissolving known amount of microparticles in 1-N-allyl-3-methylimidazolium chloride (AMIMCI). Solutions were diluted with DMSO and analyzed by suitable HPLC method. The total drug loading in dry microparticles includes all the drug material present in the powder product, i.e. the tightly bound encapsulated drug, the weakly bound drug adsorbed inside the cavities on the particle surface and the non-encapsulated drug that had dried separately. Non-bound fraction of the drug presents the drug that had either spray dried separately or loosely bound drug that was released within 30 min in dissolution medium.

TABLE 9

| Sample | Yield (%) | Total loading (%) | Non-bound fraction (%) | Final loading (%) |
|---|---|---|---|---|
| INDO20 | 29.5 | 19.5 | 73.2 | 6.1 |
| INDO30 | 20.2 | 28.8 | 70.1 | 12.2 |
| INDO40 | 19.2 | 40.3 | 74.1 | 15.1 |
| METO20 | 31.3 | 17.1 | 81.2 | 4.5 |
| METO30 | 30.9 | 23.9 | 85.1 | 5.1 |
| METO40 | 29.2 | 34.2 | 87.5 | 7.7 |
| VERA20 | 33.7 | 17.2 | 81.8 | 4.5 |
| VERA30 | 28.4 | 27.3 | 79 | 5.4 |
| VERA40 | 29.3 | 38.1 | 83.3 | 8.2 |
| NADO20 | 33.5 | *20 | 87.4 | **3.6 |
| NADO30 | 35.2 | *30 | 95.6 | **1.8 |
| NADO40 | 25.7 | *40 | 96.8 | **2.4 |
| IBU20 | 23.2 | 11.7 | 84.5 | 1.65 |
| ATE20 | 31.6 | *20 | 95.7 | **1.06 |

*Theoretical loading used as total loading
**Final loading calculated from theoretical total loading Final loading presents the amount of drug that has been either bound to NFC by hydrogen bonding or physically entrapped inside of the particles. Details of the drug loadings for each batch are given in Table 9, where the yield, total loading, non-bound fraction and final loading of spray dried particles as mass percents is presented. Indomethacin microparticles had the highest final loading that was in range from 6.1 to 15.1% while in case of metoprolol and verapamil particles these values were between 4.5 and 8.2%. Powders containing those three drugs were chosen for further studies. Particles containing ibuprofen had the lowest total loading of 11.7% due to the combination of high inlet temperature and low melting point of ibuprofen (Table 9) that caused high portion of the drug to melt and adhere to the walls, resulting in unacceptable drying. In case of nadolol and atenolol low values of final loading that were in range of 1.06 to 3.6% could be explained as consequence of limited drug water solubility that caused precipitation of drug in feeding suspension after addition of NFC. This caused high fraction of drug to dry separately.

However the main difference in final loading is most probably due to different affinity of drugs for cellulose fibers. It has been shown that drugs may bind directly to the surface of cellulose crystals and that ionic interactions as well as choice of dispersion medium have important role in binding process. In our study aqueous solution of $NH_3$ was used as solvent for indomethacin causing negative charge while metoprolol and verapamil were positively charged since their salts were used.

Figure 16:
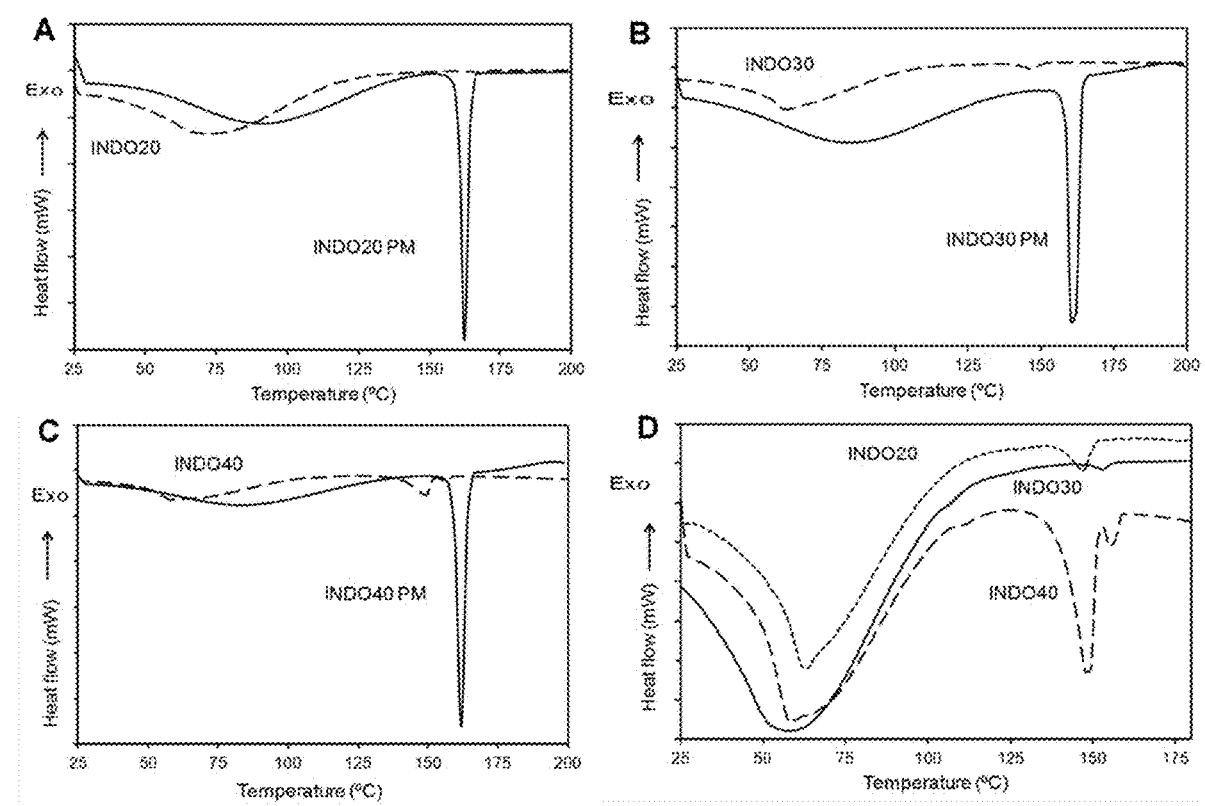
FIG. 16 shows DSC curves of NFC microparticles containing indomethacin A) INDO20, B) INDO30, C) INDO40 compared to corresponding physical mixtures and D) curves of microparticles INDO20, NDO30, and INDO40.
Figure 17:
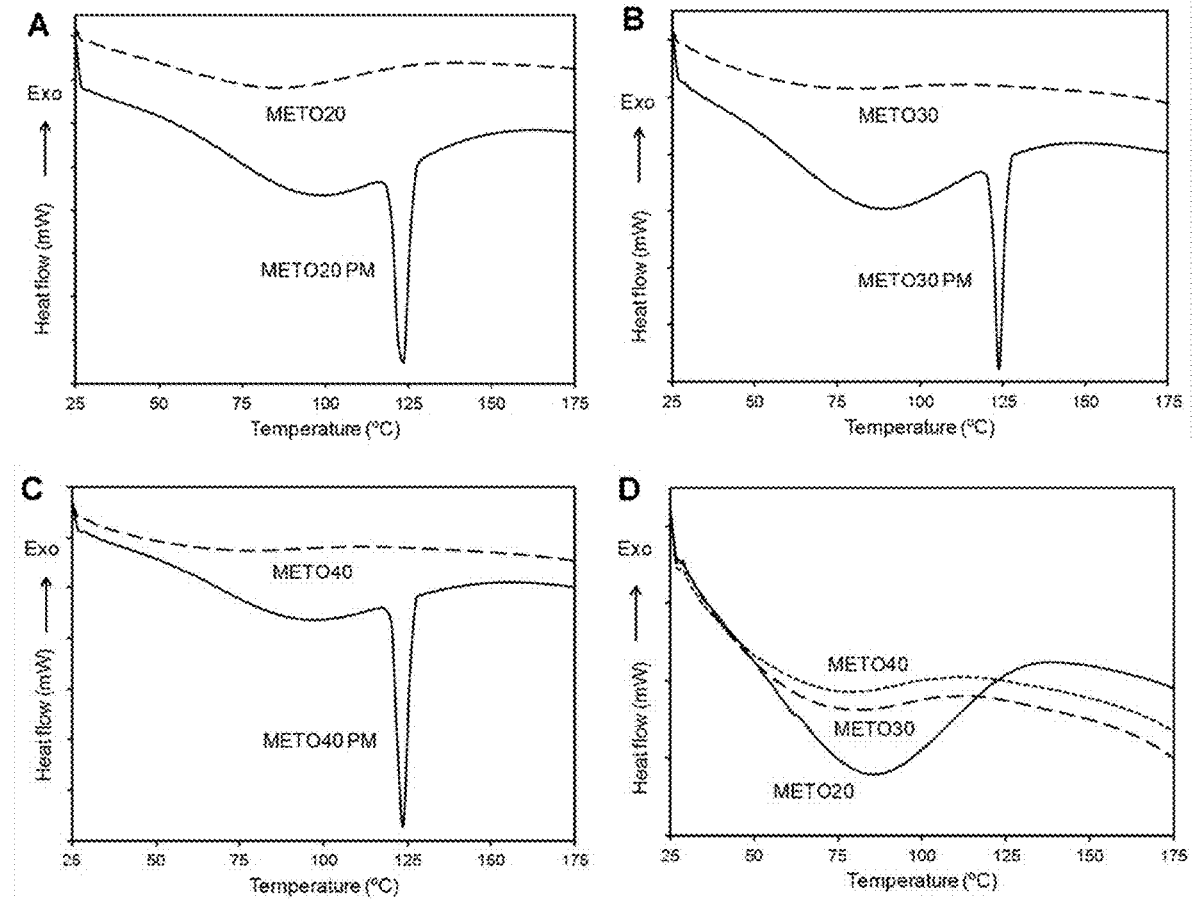
FIG. 17 shows DSC curves of NFC microparticles containing metoprolol A) METO20 B) METO30 C) METO40 compared to corresponding physical mixtures and D) curves of microparticles METO20, METO30, and METO40.

Differential scanning calorimetry of spray dried particles, physical mixtures of NFC and of tested drugs was carried out. The physical mixtures were prepared mixing spray dried NFC powder and drug in ratio that corresponded to the ratio in drug loaded particles. The samples were placed in aluminum pans and heated at a scanning rate of 10° C./min between 25-200° C. The physical state of the drugs inside the dry particles was assessed by thermal analysis. The DSC thermal profiles of produced powders are compared to the corresponding drug-NFC physical mixtures (FIGS. 16 and 17). The DSC curves of INDO20, INDO30 and INDO40 (FIG. 16) show broad endothermic peaks in the temperature range of 58° C. to 100° C., which is related to the loss of water retained in the samples after spray drying process. For physical mixtures, sharp peaks are observed at the temperature that corresponds to melting of crystalline form γ of indomethacin. For spray dried particles the peak is shifted to a lower temperature and peak intensity is significantly decreased. The position of the peak reveals that indomethacin is present in a form and peak intensity that its crystallinity is decreased. The production conditions, which involved the use of 50 mM $NH_4OH$ as the solvent and high temperature during the drying, caused small portion of the drug has remained in the crystalline state. Transformation of crystalline form γ which melting temperature is 160-164° C. to form α with melting point 153-155° C. has occurred. However the drug in the final product is mainly in the amorphous state. Similar results were obtained in case of metoprolol (FIG. 17) and verapamil (data not shown). Sharp melting peak seen in the physical mixtures disappears in spray dried products, indicating that drugs are also in the amorphous state after the production process. These results are in accordance with literature data that reports spray drying process to produce amorphous materials.

Figure 18:
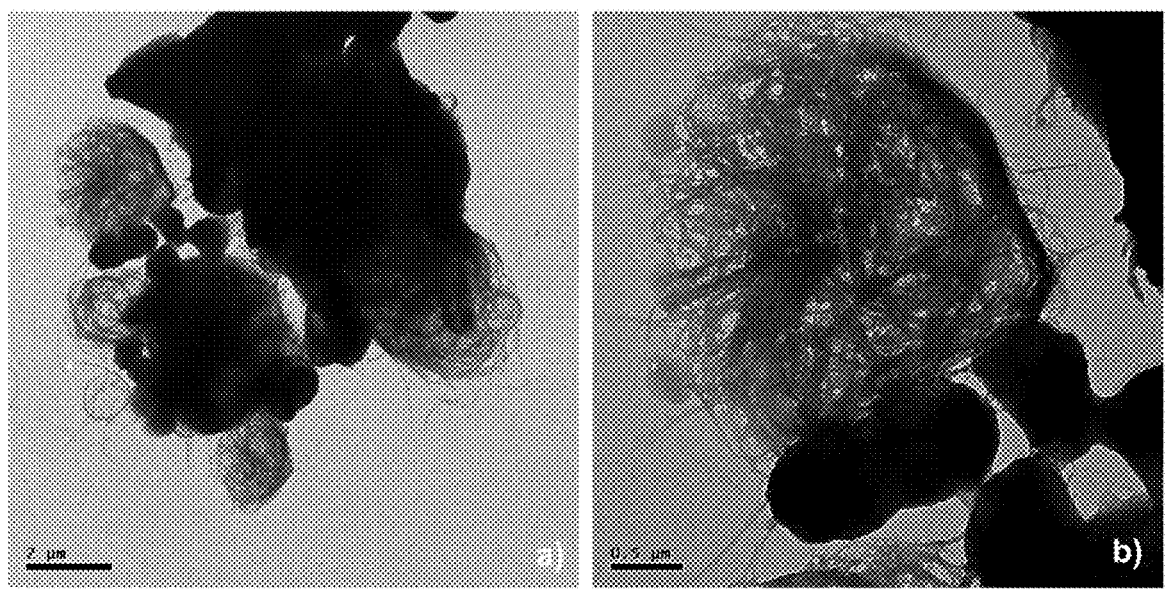
FIG. 18 shows TEM images of microparticles containing indomethacin (INDO20) after non-bound fraction was released with lower a) and higher b) magnification.
Figure 19:
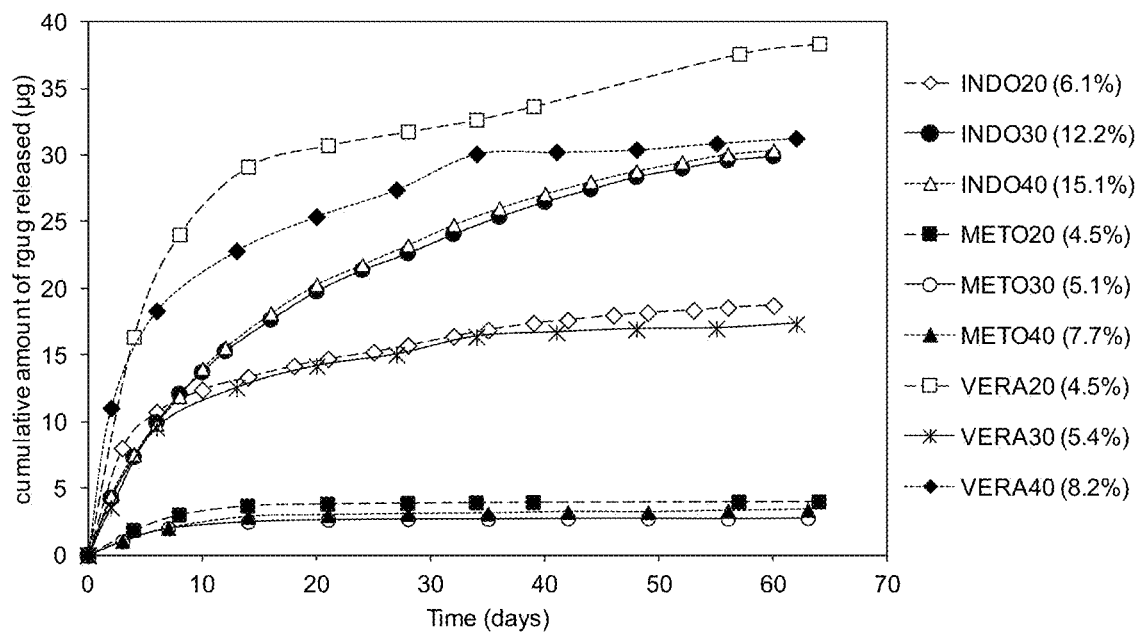
FIG. 19 shows drug release curves from indomethacin, metoprolol tartrate and verapamil hydrochloride loaded NFC microparticles.
Figure 20:
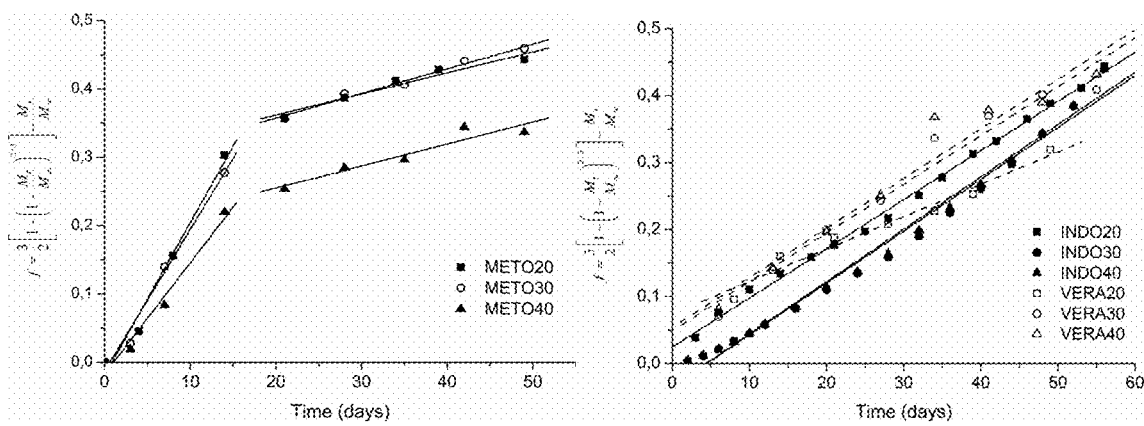
FIG. 20 shows plots of a function of dissolved fraction of the drug as per eq (6) against the dissolution time for (left) metoprolol and (right) indomethacin and verapamil. Linear regions indicate diffusion controlled release and lines are best fits to the data points.

For dissolution studies 40 mg of microparticles was placed on hydrophilic polypropylene membrane with pore size 0.2 μm and washed with 400 ml of medium using vacuum filtration system. In case of metoprolol tartrate, verapamil hydrochloride, nadolol and atenolol deionized water was used as medium and for indomethacin and ibuprofen phosphate buffer pH 7.4 was chosen as medium based on drugs solubility. This step was performed in order to remove non-bound fraction of drug. Concentration of drug in medium was measured by suitable HPLC method to quantify non-bound drug fraction. After non-bound fraction was removed samples were transferred to 50 ml glass bottles with 10 ml of medium and placed into the shaking water bath equipped with the tray for erlenmeyer flasks. Shaking frequency was set at 110 $min^{-1}$. The samples (0.3 ml) were taken at various time points and centrifuged at 12000 rpm for 5 min. The supernatant was analyzed by suitable HPLC method to determine released amount of drug and sedimented microparticles were resuspended in the medium and placed back in the bottles. For analyzing releasing kinetics results of dissolution test were fitted to mathematical model developed by Baker and Lonsdale. The dissolution test was performed after washing the non-bound fraction of drug. The non-bound fraction is relatively high and presents the fraction of drug that was spray-dried separately as well as weakly bound fraction easily accessible to water. FIG. 18 shows particle appearance after non-bound drug fraction was released. The shown particles are loaded with indomehacin (INDO 20) and non-bound fraction in this case was 73.2%. Picture shows that certain portion of particles appear as highly porous fibrous structure after they released weakly bound fraction. FIG. 19 presents the dissolution profiles of microparticles containing 6.1%, 12.2%, 15.1% of indomethacin, 4.5%, 5.1%, 7.7% of metoprolol and 4.5%, 5.4%, 8.2% of verapamil. After this burst phase in release the dissolution profiles are characterized by extremely slow release rate that is the consequence of the releasing tightly bound fraction of the drug (FIG. 19). Dissolution curves were fitted a mathematical model describing drug releasing kinetics from a spherical matrix developed by Baker and Lonsdale (Baker et al., 1974). The dissolution rate is given by the equation:

$$\frac{3}{2}\left[1-\left(1-\frac{M_t}{M_\infty}\right)^{2/3}\right]-\frac{M_t}{M_\infty}=\frac{3D_mC_{ms}}{r_0^2C_0}t \quad (5)$$

where $M_t$ is the drug released amount at time t and $M_\infty$ is the amount of drug released at an infinitive time, $D_m$ is the effective diffusion coefficient of the drug inside the particle, $C_{ms}$ is the drug solubility in the matrix, $r_0$ is the radius of the spherical matrix and $C_0$ is the initial concentration of drug in the matrix. The equation (5) can be rearranged as following:

$$f=\frac{3}{2}\left[1-\left(1-\frac{M_t}{M_\infty}\right)^{2/3}\right]-\frac{M_t}{M_\infty}=kt \quad (6)$$

where the release constant k, corresponds to the slope of the curves obtained when the left side of the equation (f) is plotted against time (FIG. 20).

In case of METO20 and VERA20, the plots in FIG. 20 consist of two distinctive parts where the first part corresponds to one or two weeks periods respectively. Particles in this period show different release kinetics than later during the dissolution. This is probably due to the release of a drug fraction located close to the particle surface or a loosely bound fraction. After this part has been released, pronounced reduction in drug release rate can be seen.

During the second period the drug is released by diffusion through the matrix system. The two-phase phenomenon was not visible in particles containing indomethacin where constant slope was obtained throughout the dissolution. The difference in the shape of the dissolution curves could be the consequence of different solubility in dissolution medium. Indomethacin has lower solubility that causes slower release of loosely bound fraction during the first two weeks. Table 10 gives values of coefficients of determination and slopes for all the batches slopes from the fits shown in FIG. 7, for spray dried particles containing indomethacin, metoprolol and verapamil. The release rate constant k for all three indomethacin samples has similar values, which indicates that drug loading does not have influence on the diffusion rate.

TABLE 10

| | $r^2$ | slope (k) |
|---|---|---|
| INDO20 | 0.994 | $1.83 \times 10^{-7}$ |
| INDO30 | 0.995 | $1.88 \times 10^{-7}$ |
| INDO40 | 0.994 | $1.78 \times 10^{-7}$ |
| VERA20 | 0.994 | $5.85 \times 10^{-7}$ |
| METO20 | 0.905 | $1.00 \times 10^{-9}$ |

Further, solubility of the drug in the dissolution medium did not primarily determine the diffusion rate since VERA20 sample has significantly higher k values than METO20 and both drugs are freely soluble in water (Table 9). Also, the solubility of indomethacin is very low compared to verapamil and metoprolol, but its dissolution rate was still between that of VERA20 and METO20. Therefore the difference in the diffusion rate is most probably due to different affinity of drugs for NFC.

NFC has strong affinity to water, which makes drying it difficult. The residence time in the spray-drying chamber is short and therefore high temperature needs to be used in drying. If lower temperature and/or higher feeding rates were to be used, the wet material would adhere to the chamber. The application of high temperature when spray drying the aqueous suspension of NFC containing an API, increases the risk of degradation of the API during the drying process. High temperature is also a limitation for the choice of the API if its melting point is low (Table 11, showing the values of melting point ($T_m$), water solubility and stability in water solution of tested drugs). Generally, particles reach a maximum temperature during spraying, which is 15-20° C. below the outlet temperature of a co-current dryer. During the particle production outlet temperatures were in the range of 120-127° C., which was sufficient for successful drying.

TABLE 11

| API | Solubility in water | $T_m$ (° C.) | Stability in water solution (21° C.) |
|---|---|---|---|
| Indomethacin | <1 µg/ml ↑ with ↑ pH <1 mg/ml | 158-165 | *pH 7.4 up to 4 days |
| Ibuprofen | 6 mg/ml (50 mM NH₄OH) | 75-78 | / |
| Nadolol | *6.77 mg/ml | 124-136 | *up to 30 days |
| Atenolol | 26 mg/ml | 146-148 | / |
| Metoprolol tartrate | freely | 120-122 | *up to 60 days |
| Verapamil hydrochloride | freely | 140-144 | *up to 7 days |

*Values obtained from testing

The second limitation step of spraying process is API's solubility to the spraying fluid (Table 11). In the present work, the spray-dryer was limited to aqueous solvents. Therefore in case of atenolol, nadolol, metoprolol tartrate and verapamil hydrochloride, water was used as the solvent whereas indomethacin and ibuprofen were dissolved in 50 mM aqueous NH₄OH. NH₄OH was chosen as solvent since NH₃ is removed as gas during the drying process due to the high temperature in the drying chamber. In all cases, the solid content in the feeding suspension was kept at 0.5% since higher concentrations caused clogging of spray nozzle due to the high viscosity. The employed method resulted in the production of white powders with the exception of indomethacin, which resulted in yellow powder. The colour is a consequence of yellow amorphous indomethacin. The intensity of powder colour increased with increasing amount of indomethacin. The yield was in the range of 19-35% since a lot of the material adhered to the drying chamber. High temperature induces melting of the drug inside the chamber causing powder stickiness and adherence resulting in low yields.

While the invention has been described with respect to specific examples including presently preferred modes of carrying out the invention, those skilled in the art will appreciate that there are numerous variations and permutations of the above described embodiments that fall within the spirit and scope of the invention. It should be understood that the invention is not limited in its application to the details of construction and arrangements of the components set forth herein. Variations and modifications of the foregoing are within the scope of the present invention.

The invention claimed is:

1. A delivery system for sustained delivery of bioactive agents, wherein said system comprises:
    a hornificated nanofibrillated cellulose hydrogel matrix comprised of mechanically disintegrated native non-ionic grade nanofibrillated cellulose derived from plant based material, wherein the nanofibrillated cellulose comprises microfibrils and microfibril bundles, the microfibrils having a length exceeding 1 µm and a number average diameter below 200 nm and the microfibril bundles having a diameter less than 1 µm, said hydrogel matrix entrapping particles of at least one bioactive agent, wherein the amount of bioactive agent is about 25-60 wt % calculated based on dry weight of the matrix and the matrix has a predefined thickness depending on a dosage form; and
    at least one support comprising synthetic polymers, wherein the hydrogel matrix is incorporated in or on the at least one support.

2. The delivery system according to claim 1, wherein the system is selected from the group consisting of a medical device, implant, transdermal patch or a formulation for oral, sub-lingual, topical, intraocular, intestinal, rectal, subcutaneous, parenteral or mucoadhesive application.

3. The delivery system according to claim 1, wherein the system is selected from the group consisting of an intrauterine delivery system or vaginal delivery system or subcutaneous implant.

4. The delivery system according to claim 1, wherein said matrix comprises from 0.1 to 99.9 wt % of nanofibrillated cellulose.

5. A method for sustained delivery of bioactive agents to a subject, comprising administering the delivery system according to claim 1 to provide a sustained delivery of the at least one bioactive agent.

6. The method according to claim 5, wherein the delivery system is selected from the group consisting of a medical device, an implant, a transdermal patch, or a formulation for oral, sub-lingual, topical, intraocular, intestinal, rectal, subcutaneous, parenteral or mucoadhesive application.

7. The method according to claim 5, wherein the delivery system is selected from the group consisting of an intrauterine delivery system or vaginal delivery system or subcutaneous implant.

8. The delivery system according to claim 1, wherein the nanofibrillated cellulose provides a controlled swelling of up to about 10% of the matrix.

9. The delivery system according to claim 1, wherein the thickness of the matrix is further dependent on the concentration of the nanofibrillated cellulose.

10. The delivery system of claim 1, wherein the nanofibrillated cellulose acts as a carrier of the bioactive agent.

11. The delivery system of claim 1, further comprising a cellulolytic enzyme providing enzymatic degradation of the nanofibrillated cellulose.

12. The delivery system of claim 1, wherein the matrix forms a reservoir for the bioactive agent, the size and/or shape of the reservoir corresponding with at least one of a desired dosage, amount, activity, or release time of the bioactive agent.

13. The delivery system according to claim 1, wherein the thickness of the support is about 0.01 to about 1.0 mm.

14. The delivery system of claim 1, wherein swelling of the hydrogel matrix coated with the support generally takes place in only one direction.

15. The delivery system of claim 1, wherein the bioactive agent particles are selected from a prophylactic agent, a drug substance, or a combination thereof.

16. The delivery system of claim 12, wherein the reservoir encases the hydrogel matrix.

17. The delivery system of claim 1, wherein the hydrogel matrix is configured to entrap and to control release the particles of the at least one bioactive agent.

* * * * *

UNITED STATES PATENT AND TRADEMARK OFFICE
CERTIFICATE OF CORRECTION

| | | |
|---|---|---|
| PATENT NO. | : 11,389,537 B2 | Page 1 of 1 |
| APPLICATION NO. | : 14/358141 | |
| DATED | : July 19, 2022 | |
| INVENTOR(S) | : Antti Laukkanen et al. | |

It is certified that error appears in the above-identified patent and that said Letters Patent is hereby corrected as shown below:

On the Title Page

At (72) Inventors, please delete "Prijo Kortesuo" and insert --Pirjo Kortesuo-- therefor.

Signed and Sealed this
First Day of November, 2022

Katherine Kelly Vidal
*Director of the United States Patent and Trademark Office*